(12) United States Patent
Loiret-Bernal et al.

(10) Patent No.: US 8,235,302 B2
(45) Date of Patent: Aug. 7, 2012

(54) IDENTIFICATION FEATURES

(75) Inventors: Cedric Loiret-Bernal, Evanston, IL (US); Linette Demers, Evanston, IL (US); Bjoern Rosner, Chicago, IL (US); Michael Nelson, Libertyville, IL (US); Ray Eby, Grays Lake, IL (US); Joseph S. Fragala, San Jose, CA (US); Raymond Roger Shile, Los Gatos, CA (US); Hua Zhang, Evanston, IL (US); John Edward Bussan, Naperville, IL (US); Sylvain Cruchon-Dupeyrat, Chicago, IL (US)

(73) Assignee: NanoInk, Inc., Skokie, IL (US)

( * ) Notice: Subject to any disclaimer, the term of this patent is extended or adjusted under 35 U.S.C. 154(b) by 1669 days.

(21) Appl. No.: 11/109,877

(22) Filed: Apr. 20, 2005

(65) Prior Publication Data
US 2010/0294844 A1    Nov. 25, 2010

Related U.S. Application Data

(60) Provisional application No. 60/563,443, filed on Apr. 20, 2004.

(51) Int. Cl.
G06K 19/06 (2006.01)
B30B 15/34 (2006.01)
(52) U.S. Cl. .......................... 235/494; 100/38
(58) Field of Classification Search .................. None
See application file for complete search history.

(56) References Cited

U.S. PATENT DOCUMENTS

| | | | |
|---|---|---|---|
| 3,272,118 A | 9/1966 | Ackley et al. | |
| 4,189,996 A | 2/1980 | Ackley et al. | |
| 4,548,825 A | 10/1985 | Voss et al. | |
| 4,574,694 A | 3/1986 | Dubuit | |
| 4,591,279 A | 5/1986 | Speicher et al. | |
| 5,006,362 A | 4/1991 | Hilborn | |
| 5,023,437 A | 6/1991 | Speicher et al. | |
| 5,118,369 A | 6/1992 | Shamir | |
| 5,376,771 A | 12/1994 | Roy | |
| 5,457,895 A | 10/1995 | Thompson et al. | |
| 5,512,131 A | 4/1996 | Kumar et al. | |
| 5,529,767 A | 6/1996 | Brox et al. | |

(Continued)

FOREIGN PATENT DOCUMENTS

WO    WO 2004/040505    5/2000

(Continued)

OTHER PUBLICATIONS http://www.merriam-webster.com/dictionary/stamp, printed Dec. 31, 2010, pp. 1-2.*

(Continued)

Primary Examiner — Shanon A Foley
(74) Attorney, Agent, or Firm — Foley & Lardner LLP

(57) ABSTRACT

Methods for providing pharmaceutical compositions and objects with identification regions and identification features which are difficult to detect. Microlithography, nanolithography, and stamping methods are used. The identification features can be positive protrusions or negative indentations with respect to the surface. The identification regions can comprise bar codes and holograms. DPN printing or other lithographies such as electron beam lithography, optical lithography, or nanoimprint lithography can be used to prepare stamps, which are then used to prepare the identification features. Redundant patterns can be formed. The invention is useful for counterfeit prevention. An apparatus for stamping the identification features is also described.

24 Claims, 16 Drawing Sheets

U.S. PATENT DOCUMENTS

| | | | |
|---|---|---|---|
| 5,618,760 | A | 4/1997 | Soh et al. |
| 5,620,850 | A | 4/1997 | Bamdad et al. |
| 5,630,449 | A | 5/1997 | Ammann et al. |
| 5,700,998 | A * | 12/1997 | Palti .............................. 235/375 |
| 5,772,905 | A | 6/1998 | Chou |
| 5,845,264 | A | 12/1998 | Nellhaus |
| 5,878,658 | A | 3/1999 | Ackley |
| 5,907,144 | A | 5/1999 | Poon et al. |
| 5,992,742 | A | 11/1999 | Sullivan et al. |
| 6,286,421 | B1 | 9/2001 | Ackley |
| 6,309,580 | B1 | 10/2001 | Chou |
| 6,314,876 | B1 | 11/2001 | Ackley |
| 6,450,089 | B2 | 9/2002 | Ackley |
| 6,481,347 | B2 | 11/2002 | Ackley |
| 6,481,753 | B2 | 11/2002 | Van Boom et al. |
| 6,482,742 | B1 | 11/2002 | Chou |
| 6,518,189 | B1 | 2/2003 | Chou |
| 6,543,692 | B1 | 4/2003 | Nellhaus et al. |
| 6,635,311 | B1 | 10/2003 | Mirkin et al. |
| 6,642,129 | B2 | 11/2003 | Liu et al. |
| 6,656,398 | B2 | 12/2003 | Birch et al. |
| 6,692,030 | B1 | 2/2004 | Phillips |
| 6,696,220 | B2 | 2/2004 | Bailey et al. |
| 6,719,915 | B2 | 4/2004 | Willson et al. |
| 6,776,340 | B2 | 8/2004 | Murokh et al. |
| 6,776,341 | B1 | 8/2004 | Sullivan et al. |
| 6,799,725 | B1 | 10/2004 | Hess et al. |
| 6,827,979 | B2 | 12/2004 | Mirkin et al. |
| 6,882,738 | B2 | 4/2005 | Davis et al. |
| 7,225,082 | B1 * | 5/2007 | Natan et al. ...................... 702/27 |
| 2002/0122873 | A1 | 9/2002 | Mirkin et al. |
| 2003/0068446 | A1 | 4/2003 | Mirkin et al. |
| 2003/0162004 | A1 | 8/2003 | Mirkin et al. |
| 2003/0185967 | A1 | 10/2003 | Eby et al. |
| 2003/0236219 | A1 | 12/2003 | Nightingale |
| 2004/0026684 | A1 | 2/2004 | Empedocles |
| 2004/0170725 | A1 * | 9/2004 | Begleiter ........................ 426/87 |
| 2004/0175631 | A1 | 9/2004 | Crocker et al. |
| 2005/0018013 | A1 | 1/2005 | Nelson et al. |
| 2005/0035983 | A1 | 2/2005 | Cruchon-Dupeyrat et al. |
| 2010/0294146 | A1 | 11/2010 | Fragala et al. |
| 2010/0294147 | A1 | 11/2010 | Loiret-Bernal et al. |
| 2010/0294927 | A1 | 11/2010 | Nelson et al. |
| 2010/0297027 | A1 | 11/2010 | Loiret-Bernal et al. |
| 2010/0297190 | A1 | 11/2010 | Loiret-Bernal et al. |
| 2010/0297228 | A1 | 11/2010 | Loiret-Bernal et al. |

FOREIGN PATENT DOCUMENTS

| | | |
|---|---|---|
| WO | WO 00/41213 A1 | 7/2000 |
| WO | WO 01/10464 A1 | 2/2001 |
| WO | WO 01/91855 A1 | 12/2001 |
| WO | WO 2005/004797 | 1/2005 |

OTHER PUBLICATIONS

Berman (Journal of Medical Systems. Feb. 2004; 28 (1): 9-29).*
U.S. Appl. No. 10/307,515, filed Dec. 2, 2002, Mirkin et al.
U.S. Appl. No. 10/375,060, filed Feb. 28, 2003, Cruchon-Dupeyrat et al.
Chou et al., "Imprint of sub-25 vias and trenches in polymers," Applied Physics Letters, vol. 67, No. 21, (Nov. 1995).
Chou et al., "Nanoimprint lithography," J. Vac. Sci. Technol. B, vol. 14, No. 6, (Nov./Dec. 1996).
"FDA's Counterfeit Drug Task Force Interim Report," (Oct. 2003).
"FDA's Combating Counterfeit Drugs Report," (Feb. 2004).
Harmening et al., Proceedings IEEE Micro Electro Mechanical Systems pp. 202-207, (1992).
Li et al., "Molding of Plastic Components Using Micro-Dem Tools," Electronics Manufacturing Technology Symposium, pp. 145-149, (1992).
Madou, *Fundamentals of Microfabrication, The Science of Miniaturization*, Second Edition, CRC Press, USA, Chapters 1-4, (2002).
Pique et al., *Direct-Write Technologies for Rapid Prototyping Applications: Sensors, Electronics, and Integrated Power Sources*, Academic Press, San Diego CA, Ch. 10 & pp. 617-619, (2002).
Sun et al., "Multilayer resist methods for nanoimprint lithography on nonflat surfaces," J. Vac. Sci. Technol. B, vol. 16, No. 6, pp. 3922-3925, (Nov./Dec. 1998).
Tan et al., "Roller nanoimprint lithography," J. Vac. Sci. Technol. B, vol. 16, No. 6, pp. 3926-3928, (Nov./Dec. 1998).
Zhang et al., "DPN-Generated Nanostructures Made of Gold, Silver, and Palladium," Chem. Mater., vol. 16, No. 8, pp. 1480-1484, (2004).
Zhang et al., "Biofunctionalized Nanoarrays of Inorganic Structures Prepared by Dip-Pen Nanolithography," Nanotechnology, vol. 14, pp. 113-117, (2003).
Zhang et al., "Dip-Pen nanolithography-Based Methodology for Preparing Arrays of Nanostructures Functionalized with Oligonucleotides," Advanced Materials, vol. 14, No. 20, pp. 1472-1474, (Oct. 16, 2002).

* cited by examiner

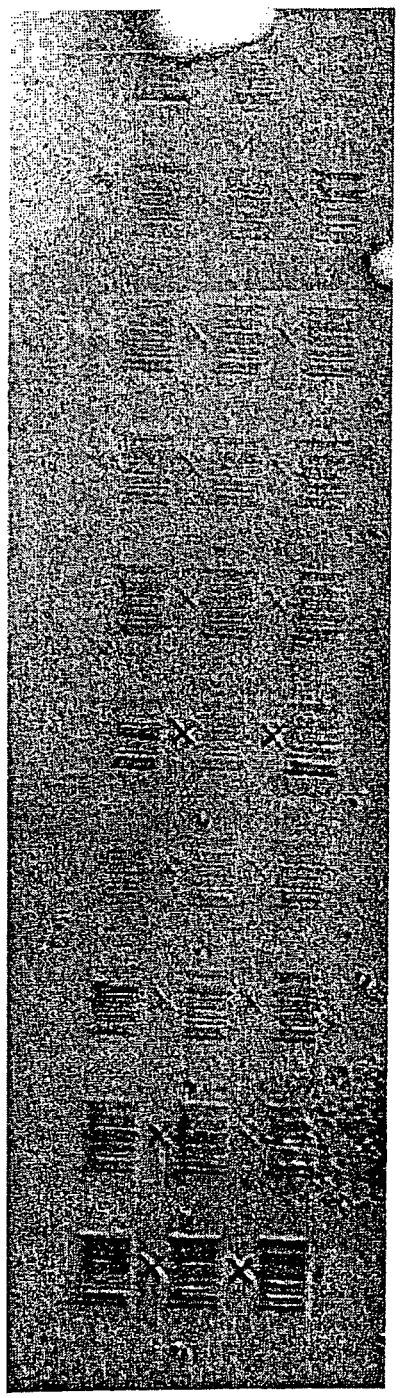
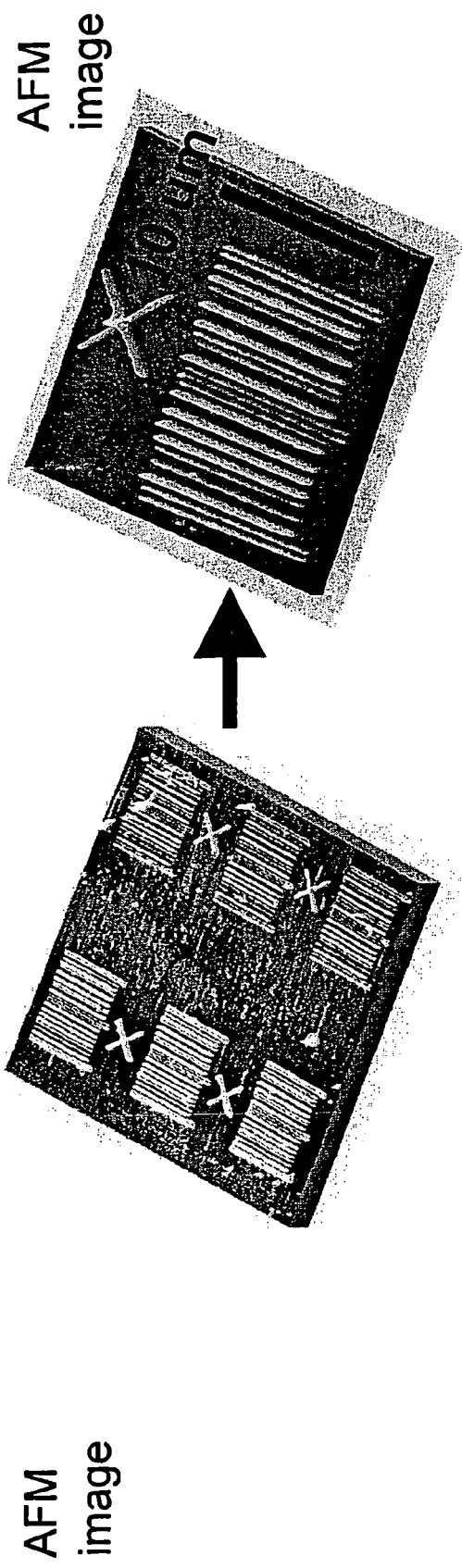
Optical image
AFM image
30 barcode regions on a stamp
AFM image
- Silicon stamps with barcode pattern repeated 30 times.
- Line widths: 150/200/250 nm
Figure 3

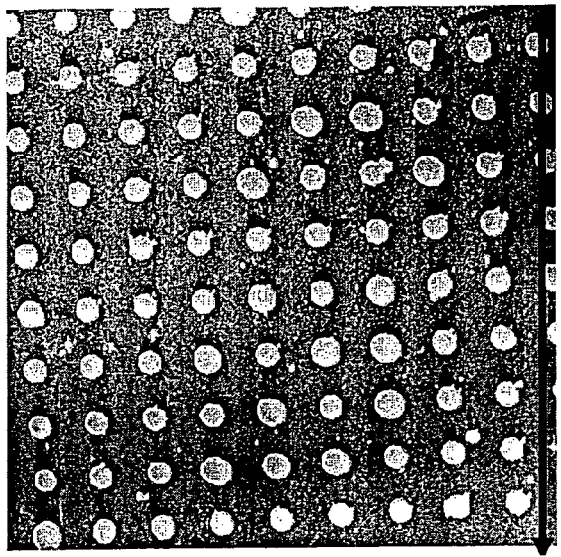
Silicon relief structures:
Height ~130 nm
Width: 5 um
Pitch: 10 um
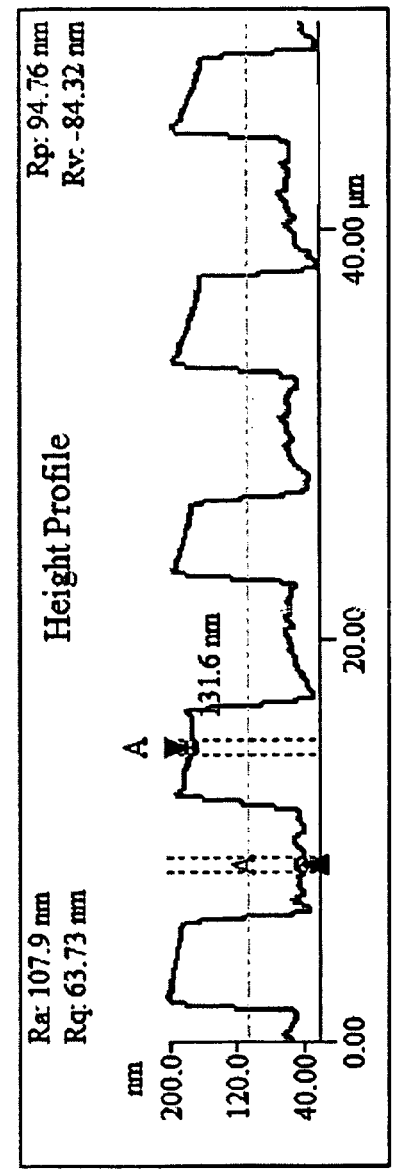
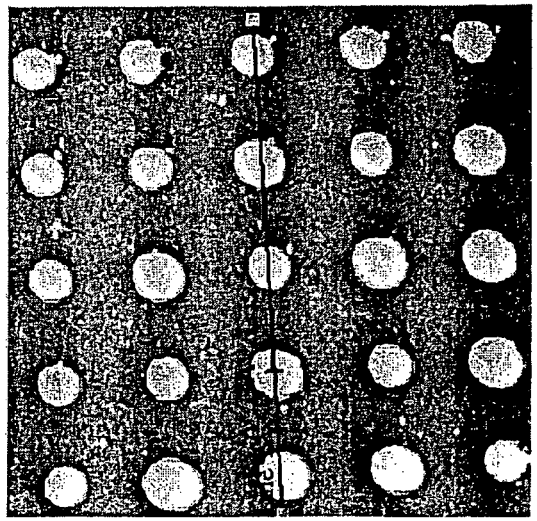
Figure 6

Design window in InkCAD: Each DPN pen was to write 3 patterns. Different colors refer to different pens that write in parallel.

After stamping, a tablet has a small visible mark where the stamp pressed slightly into the tablet coating. The surface of the impression is smooth and reflective.

IDENTIFICATION FEATURES

RELATED APPLICATIONS

This application claims priority to U.S. provisional patent application Ser. No. 60/563,443 filed Apr. 20, 2004 to Loiret-Bernal et al. entitled "Identification Features", which is hereby incorporated by reference in its entirety including the specification, working examples, figures, and claims.

FIELD OF INVENTION

The present invention relates generally to objects and compositions having identification regions and identification features which are difficult to detect, particularly with the naked eye. In particular, pharmaceutical compositions are of interest which have microscale and nanoscale identification regions and features such as bar codes and holograms which comprise dots, lines, or other geometric figures.

BACKGROUND OF THE INVENTION

Methods are known for providing objects and compositions including food and pharmaceutical compositions with identification. See, for example, U.S. Pat. Nos. 4,189,996; 4,548,825; 5,006,362; 5,118,369; 5,376,771; 5,457,895; and 5,529,767. U.S. Pat. No. 6,481,753 to Van Boom et al. describes use of thermochromic inks to print variable confidential information for use in detection of copying or scanning. U.S. Pat. No. 6,692,030 to Phillips describes use of nanopatterns on a substrate for use in detecting copying. In many cases, however, prior methods have not been experimentally verified, or poorly demonstrated, and are generally inadequate for addressing present needs for identification. In particular, present identification needs have accelerated in view of heightened security concerns because of terrorism. Moreover, the economics of pharmaceutical development, especially, has resulted in expensive pharmaceuticals which can have price variation from country to country. This can encourage counterfeit and illegal trade activities. Also, governmental concern for health in view of drug counterfeiting is increasing.

Hence, a present need exists to provide objects and compositions, particularly pharmaceutical compositions, with microscale and nanoscale identification features which are difficult to detect, particularly with the naked eye or simple low resolution magnification methods such as a conventional magnifying glass. Technology is needed which can provide high throughput and is otherwise commercially attractive and in compliance with health regulations. A need also exists to develop technology wherein an identification feature can be put onto the object itself rather than a mere package for the object. In particular, the technology hurdles become great when feature sizes go from a micro scale regime into a nanoscale regime such as below one micron, and in particular, below 100 nm. In recent years, some advances in lithography have been reported but these advances have not been applied to the identification problems noted above.

In a preferred embodiment, the present invention also generally relates to nanolithography and etching, and more particularly, to systems capable of DIP PEN NANOLITHOGRAPHY™ printing (DPN™ printing) and deposition, coupled with etching and/or other methods for pattern transfer. DIP PEN NANOLITHOGRAPHY™ and DPN™ are trademarks for NanoInk, Inc., Chicago, Ill.). These methods unexpectedly can be advantageous and useful in the commercial context of counterfeit prevention.

SUMMARY OF THE INVENTION

Exemplary embodiments of the present invention are summarized in this non-limiting summary section. In one embodiment, the invention enables one to prevent counterfeiting and other fraud with use of identification features which are not generally visible to the naked eye.

In one embodiment, the invention provides a pharmaceutical composition comprising: a pharmaceutical composition having a surface, wherein the surface comprises at least one identification region, the region having at least one identification feature, the feature having a lateral dimension of about 100 microns or less.

Also provided is a pharmaceutical composition comprising: a pharmaceutical composition having a surface, wherein the surface comprises at least one identification region, the region having a plurality of identification line features, the lines having a line width of about one micron or less and a line length of at least one micron.

In another embodiment, the invention also provides an object comprising an object having a surface, wherein the surface comprises at least one identification region, the region having at least one identification feature, the feature having a lateral dimension of about 500 microns or less. In addition, the invention also provides a composition comprising: a composition having a surface, wherein the surface comprises at least one identification region, the region having at least one identification feature, the feature having a lateral dimension of about 500 microns or less.

In another embodiment, the invention further provides a method of making a pharmaceutical composition having at least one identification region and at least one identification feature comprising: (i) providing a stamp which has a surface to form at least one identification region having at least one identification feature, wherein the identification feature has a lateral dimension of about 100 microns or less; (ii) providing a pharmaceutical composition having a surface; and (iii) contacting the stamp and the pharmaceutical composition under conditions so that the pharmaceutical composition comprises a surface having the at least one identification region having at least one identification feature, wherein the identification feature has a lateral dimension of about 100 microns or less.

Still further, the invention provides a method of making a composition having at least one identification region and at least one identification feature without etching after formation of identification feature consisting essentially of: (i) providing a stamp which has a surface to form at least one identification region having at least one identification feature; (ii) providing a composition having a surface; and (iii) contacting the stamp and the composition under conditions so that the composition comprises a surface having the at least one identification region having at least one identification feature.

Also provided is an apparatus for forming identification features for pharmaceutical compositions comprising:
a pressure ram;
optionally, a stamp attached to the pressure ram for imprinting at least one identification feature on a pharmaceutical composition;
a mount for holding at least one non-wafer pharmaceutical composition;
wherein the pressure ram presses the stamp against the at least one pharmaceutical composition held by the pharmaceutical composition mount with a desired amount of force to form at least one identification feature on the at least one pharmaceutical composition.

Still other embodiments for the invention are described throughout the specification. Basic and novel features and advantages of the invention are many. For example, the identification features cannot be easily copied. Moreover, the identification features are difficult to read by copiers because specialized tools, methods, and personnel can be needed to read the identification features. High throughput is possible. Versatility can be found in the wide variety of identification features which can be formed including overt and covert embodiments. Chemicals, labels, and inks are not necessarily added to a pharmaceutical in the process of providing it with identification which is useful for governmental compliance. Small line widths can be achieved such as, for example, about 20 nm to about 50 nm, and small line separations can be achieved such as, for example, less than 50 nm or even less than 10 nm. Complex geometries can be formed including, for example, disks with smooth border, arcs, hollow circles, crossed lines without bleeding, sharp corners, and closely grouped sets of narrow features. Additional advantages can be found in the following description.

BRIEF DESCRIPTION OF THE DRAWINGS

FIG. 3 shows optical micrographs and AFM scans of barcode regions in a silicon master stamp including pattern redundancy with multiple pens.

FIG. 6 shows AFM images of micropatterns on silicon stamp, fabricated by microcontact printing and RIE.

DETAILED DESCRIPTION OF THE PREFERRED EMBODIMENTS

Figure 1:
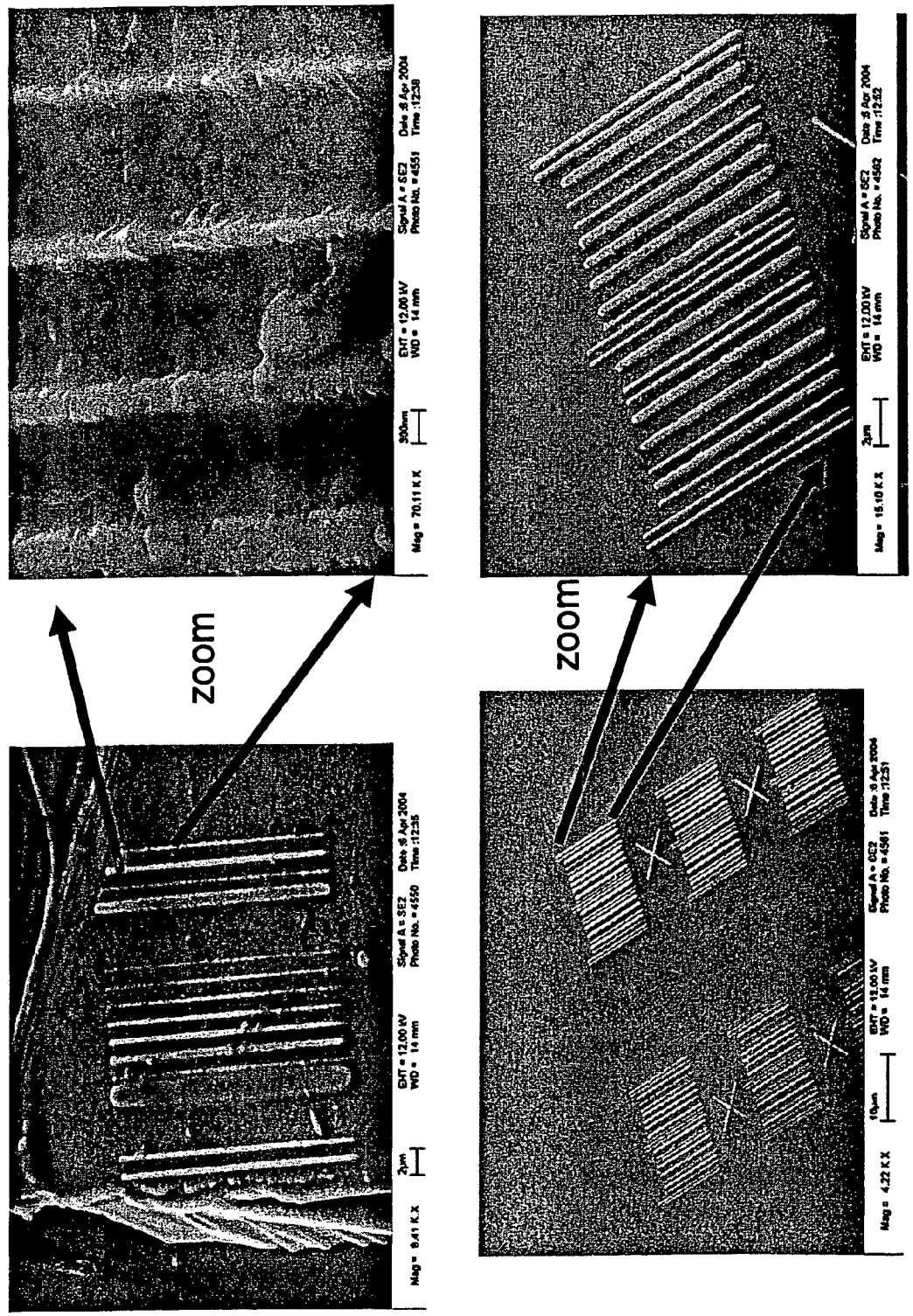
FIG. 1 shows SEM scans of a silicon master stamp.

Priority U.S. provisional patent application Ser. No. 60/563,443 filed Apr. 20, 2004 to Loiret-Bernal et al. entitled "Identification Features"which is hereby incorporated by reference in its entirety including the specification, working examples, figures, and claims.

I. Pharmaceutical Composition

The problems of pharmaceutical and drug compositions which can be subjected to counterfeiting are described in, for example, the FDA report "Combating Counterfeit Drugs" February 2004 and "FDA's Counterfeit Drug Task Force Interim Report" October 2003 and other technical literature provided in this patent application. A wide variety of pharmaceutical drugs and compositions, and there function, are known in the art and are generally described in, for example, (i) *Physicians' Desk Reference,* 49 Ed, 1995 including brand name and generic drugs, and (ii) Goodman and Gilman's, *The Pharmacological Basis of Therapeutics,* 2001. Pharmaceutical compositions can be useful for both human and animal treatment.

One embodiment of the invention comprises a pharmaceutical composition comprising: a pharmaceutical composition having a surface, wherein the surface comprises at least one identification region having at least one identification feature which has a lateral dimension of about 500 microns or less, and preferably about 100 microns or less.

The pharmaceutical composition is not particularly limited and a wide variety of pharmaceutical compositions are known in the art including pharmaceutical drugs in various shapes and sizes such as pills, tablets, caplets, capsules, and the like. Pill embossing and its variants can be the subject of the invention for pharmaceutical compositions. For example, tablets and caplets can be used after compressing or coating. Two-piece hard gelatin can be used, before or after filling with powder, gel, or liquid. Pill surface structures can include sugar shell, soft-shell, dipped or enrobed, enteric, or aqueous coated tablets, waxed tablets, and dry coatings.

The pharmaceutical compositions can contain active ingredients and passive ingredients, and in different embodiments, these can be distributed differently. The pharmaceutical composition can have an exterior region or surface which can be processed to include one or more identification regions by, for example, imprinting or embossing, whether hot or cold embossing. Hence, the pharmaceutical composition can be processible and susceptible to, for example, heat and pressure effects which allow for imprinting or embossing. The pharmaceutical composition generally can comprise an active pharmaceutical ingredient (API) but the invention is not particularly limited to how the API is distributed throughout the pharmaceutical composition. For example, the API could be in the interior or could be subjected to a coating process. A composition could be provided with the identification feature and then combined with the API. Hence, for example, the surface of the pharmaceutical composition may have little if any of the API but yet it is still part of the pharmaceutical composition. The API can be a solid, liquid, or gel API as long as the ultimate pharmaceutical composition can be processed to include the identification features described herein.

The surface of the pharmaceutical composition can be an exterior surface which represents an interface with air. In addition, however, the surface of the pharmaceutical composition could be an interior surface. For example, an interior surface can be prepared by generating a desired surface having desired surface features and then combining that surface with another composition so that the desired features are no longer directly exposed to the air but can be detected, even though they are now interior surfaces. For example, an identification region can be generated and then overcoated with a protective film, coating, or layer, which include but are not limited to thin conformal films. The surface of the pharmaceutical composition can be generally flat and smooth, although at the scale of the identification features described herein the surface can be generally rougher. Or the surface can be non-flat or curved, including spherical, oval, or bi-convex. An interior surface can be desirable to avoid scratching or rubbing of the identification region. Alternatively, the identification region may comprise one or more features, which protect the information-bearing part from erasure or damage. For example, a raised ring or frame surrounding the identification features may avoid mechanical abrasion of the identification.

The surface of the pharmaceutical composition can comprise non-identification regions and one or more identification regions. An identification region can be an area which is different from the non-identification regions and can have, for example, features for identification (identification features) which are not present in the non-identification regions. Examples of identification regions include bar codes, including for example one-dimensional or two-dimensional bar codes conforming to the standards of the Uniform Code Council. Other examples include text, symbols, holograms and other engineered patterns that can be clearly interpreted.

In many cases, a full inspection of the identification region will be needed to make the identification. In other words, only inspecting some of the identification features may not give sufficient information to provide adequate identification. For example, if a bar code identification region comprises a series of 10 lines, reading only five of the lines may not give the information needed. The identification region can be characterized by an identification region area which has an enclosing perimeter around the identification features so that all of the identification features can be found within the enclosing perimeter. This area can be for example, about 10,000 square microns or less, or about 1,000 square microns or less, or about 400 square microns or less, or about 4 square microns or less, or about one square micron or less. The identification region can be, for example a square region with a lateral length and width of 100 microns×100 microns, respectively, or 20 microns×20 microns, or 2 microns×2 microns. Or the identification region can be, for example, a generally rectangular region or circular region. In many cases, two or more identification regions are desired in case one or more of the identification regions become unreadable by scratching, rubbing, or some other undesirable event. For example, the surface can comprise more than 20, more than 30, more than 40, or more than 50 identification regions. The identification region can be sufficiently large to be seen by the naked eye or an optical microscope, even when identification features within the identification region can be sufficiently small that they cannot be seen by the naked eye or even with an optical microscope.

Identification generally can enable a recognition. Identification can be also a verification or an authentication. It can encompass both tracing and tracking as well as authentication, including both bar codes and holograms for example. For example, a pharmaceutical composition imprinted with both a micron-scale optical grating and a nanometer-scale bar code can be both uniquely authenticable by the end-user as genuine, visually, and uniquely traceable as certifiable to an origin.

The identification features are not particularly limited by any shape and can be, for example, dots, circles, lines, rectilinear structures, curvilinear structures, or bar codes, whether linear or radial. Other examples include geometric objects such as, for example, triangles or rectangles. The identification features can be space filling such as, for example, a disk or can be non-space filling such as, for example, a donut or circle with a hollowed out interior. The identification features can form holographic patterns and can be, for example, periodic arrays of lines or dots. The identification features can also form a trademark, service mark, or some other indicia of good will to the customer or branding mark. Dates, names, and other useful commercial information can be provided. In general, the identification features are not complex technological patterns such as a complex circuit pattern. Rather, in general, the function of the identification feature is for identification, not another utility. Generally, it is desired to make the feature as simple as possible while still retaining the function of being an identification feature. For example, bar code technology can be applied at this scale wherein, for example, the width, spacing, and length of lines, and ratios thereof, can be varied to provide information. Preferably, a plurality of identification features can be used and in many cases, only one identification feature is insufficient to provide the needed identification. Preferably, for example, a plurality of linear structures is used in a bar code format.

The identification features can be a positive structure with respect to the surface or a negative structure with respect to the surface. For example, a negative structure can be an indentation, whereas a positive structure can be a protrusion. Hence, for example, a line identification feature could be stamped into a surface to generate an indentation of the line, or a region of a surface could be stamped which resulted in a line protruding from the surface after stamping. Whether positive or negative, the identification feature should be durable and if a positive identification is not sufficiently durable, it can be converted to a negative identification feature.

In general, identification features are preferred which are durable over time. Identification features can be, for example, overcoated as needed to improve the durability. Durability can depend on the softness and material glass transition temperature effects of the surface. One skilled in the art can test the durability and develop conditions and surface treatments which improve durability. In general, the identification region and identification feature can be durable for a period of at least one year, for at least five years, and at least 10 years, so that the identification can be carried out even after passage of time. For example, a useful passage of time is the expiration date of a pill. In general, materials to be stamped have a glass transition temperature above about 25° C. so that at usual room temperature the material is sufficiently glassy to durably hold the identification feature. For example, the composition's glass transition temperature can be, for example, about 40° C. or more, or alternatively, about 60° C. or more, or alternatively, about 80° C. or more.

The identification regions and features can be characterized by dimensional measurements such as lateral dimensions or vertical dimensions with respect to the surface. Conventional methods can be used to measure these dimensions including methods described herein and the working examples. Conventional data processing including image processing, pattern recognition, curve fitting and optical character recognition (OCR) can be carried out to provide dimensions and average dimensions and generally to provide useful data.

The identification regions can each have one or more identification features which can be characterized by a lateral dimension with respect to the surface. The lateral dimension can be, for example, a width or a length such as, for example, a circle diameter or a line width, or the relative or absolute position compared to a known mark. The lateral dimension is different from a vertical dimension such as height. For an identification feature which is a line, the lateral dimension of length can be sufficiently long that it can be viewed with the naked eye or an optical microscope, whereas the lateral dimension which is width can be sufficiently small that it cannot be seen with a naked eye or optical microscope. The size of the lateral dimensions can be sufficiently small so that the identification features are invisible to the naked eye and difficult to detect by conventional, simple methods. Rather, difficult, relatively expensive methods can be used to detect small identification features including microscopic and nanoscopic features. At least one of the lateral dimensions can be made small. For example, the identification feature can have a lateral dimension of, for example, about 500 microns or less, or about 400 microns or less, or about 300 microns or less, or more particularly, about 250 microns or less, or more particularly, about 100 microns or less, or more particularly, about 10 microns or less. Or the identification feature can have a lateral dimension of, for example, about one micron or less, or more particularly, about 500 nm or less, or more particularly, about 250 nm or less, or more particularly, about 100 nm or less. There is no particular limit to how small the lateral dimension can be as long as the identification feature can be detected. For example, the lateral dimension can be at least about 1 nm, or more particularly, at least about 10 nm, or more particularly, at least about 100 nm, or more particularly at least about one micron. Hence, exemplary ranges for the lateral dimension include about one nm to about 500 microns, about 10 nm to about 100 nm, about 100 nm to about one micron, and about one micron to about 500 microns.

For barcodes, the line length is not particularly limited but can vary from nanoscopic to microscopic. For example, lines can be about one micron to about 50 microns long, or about 5 microns to about 25 microns long, and yet have a line width of only about 50 nm to about 150 nm wide.

The identification features can be in the form of a pattern of repeating features such as dots or lines, wherein the features are characterized by an average lateral dimension such as average circle diameter or line width. The lateral size dimensions described herein can be computed into average lateral dimensions.

The identification features can have a vertical dimension such as a height dimension or a depth dimension, and these terms are used interchangeably and for both positive structures and negative structures. The height dimension is not particularly limited and can be, for example, about five microns or less, or about one micron or less, or more particularly, about 500 nm or less, or more particularly about 250 nm or less, or more particularly about 150 nm or less. There is no particular lower limit to the height dimension as long as the identification feature can be detected. The height dimension can be, for example, about one nm or more, or about 10 nm or more, or about 25 nm or more. Exemplary ranges can be, for example, about one nm to about one micron, or about 10 nm to about 500 nm, or about 25 nm to about 250 nm. Again, if a pattern of repeating identification features are used, the vertical dimension can represent an average dimension.

In addition to the lateral dimension and the height dimension, the invention can be also characterized by a separation dimension which represents the distance between the identification features such as a separation distance or a pitch. In other words, the one or more identification features can be separated from each other by a particular distance, and this distance can be an average distance for an array of identification features. For example, if the identification features are a series of lines, a distance can be measured between the centers of the lines, or if the identification features are a series of dots, a distance can be measured between the centers of the dots. The distance of separation is not particularly limited but smaller separation distances are preferred so that the identification is invisible to the unaided eye. For example, the one or more identification features can be separated from each other by an average distance of about 500 microns or less, or more particularly, about 100 microns or less, or more particularly, about 10 microns or less, or more particularly, about one micron or less, or more particularly, about 500 nm or less.

The pharmaceutical composition can also be characterized by the density of the identification features. For example, a plurality of parallel lines can be generated wherein there is at least one line per every two microns, or at least one line per every one micron, or at least one line per every 0.5 microns. See for example FIG. 1, wherein a height profile scan be used to determine a density.

The information associated with the identification region and features may be obtained by determining one or more of the aforementioned characteristics and optionally a mathematical function or algorithm.

The surface also can comprise one or more marks which can be detected by an optical microscope or an unaided eye. The at least one mark can be located outside of the identification region. Examples include an X shaped mark. The marks, for example, can have lateral dimensions such as line width at the micron scale such as 10 microns or more, at least 50 microns or more, at least 100 microns or more.

The pharmaceutical compositions can be packaged into unit forms and used in commerce as collections of unit forms. Hence, for example, a package of a drug can be provided to a doctor or patient having, for example, 20 unit forms of the pharmaceutical composition, or a bottle with a cap can be provided having a 100 unit forms. If desired, all of the pharmaceutical compositions in unit form can be marked with at least one identification region having at least one identification feature. If desired, only selected unit forms can be marked for identification. Hence, for a large collection of unit forms, a copier may have difficulty knowing which unit form has been marked with the identification region and features. All or only a fraction of pharmaceutical compositions packaged in bulk form may include one or more of the identification region and features.

Figure 10:
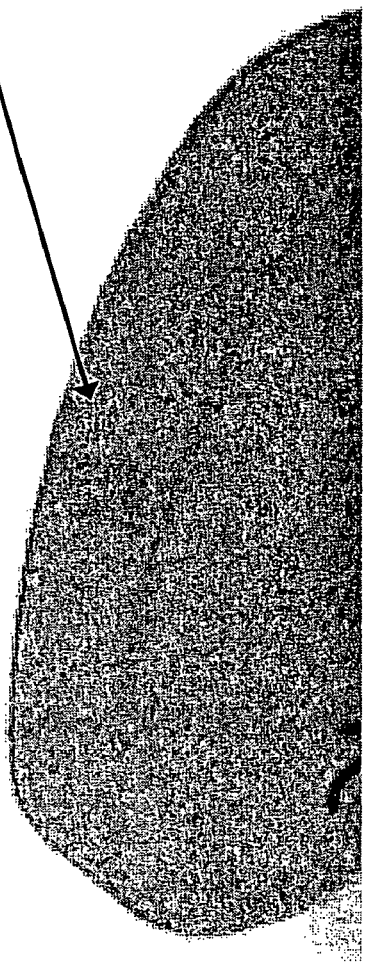
FIG. 10 shows a tablet after printing.

FIG. 10 illustrates a working example showing a tablet appearance after printing. In this working example, the tablet has a small visible mark where the stamp pressed slightly into the tablet coating. The surface of the impression is smooth and reflective. In a preferred embodiment, stamping conditions are selected so that the tablet appearance does not to the unaided eye provide a signal that it has been stamped and has identification regions or features. Even if the eye can detect that a stamp is present, however, the particular identification region and feature can be virtually impossible to copy.

Figure 7:
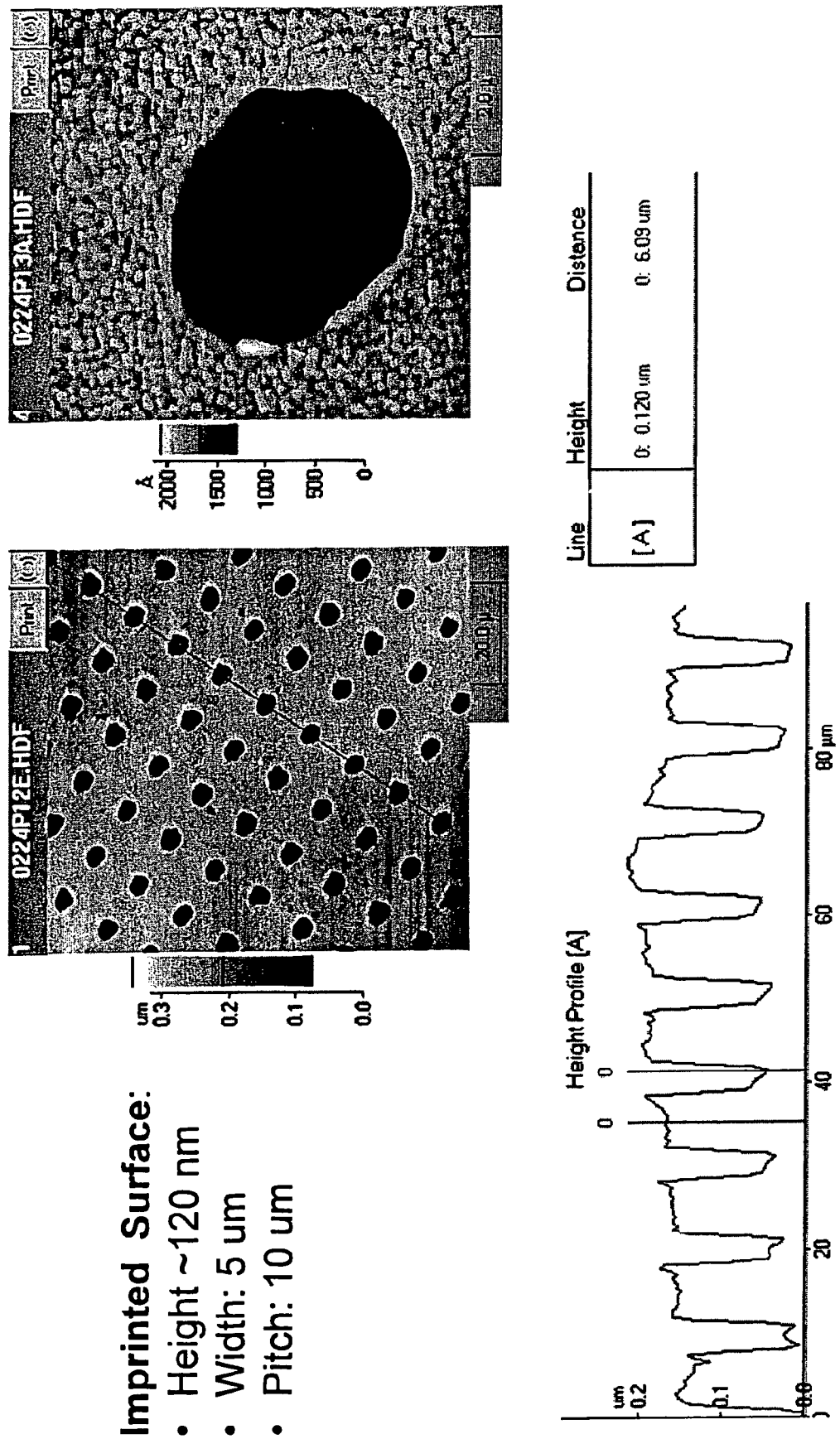
FIG. 7 shows AFM image of a micro-imprinted tablet film coating and height scans.
Figure 8:
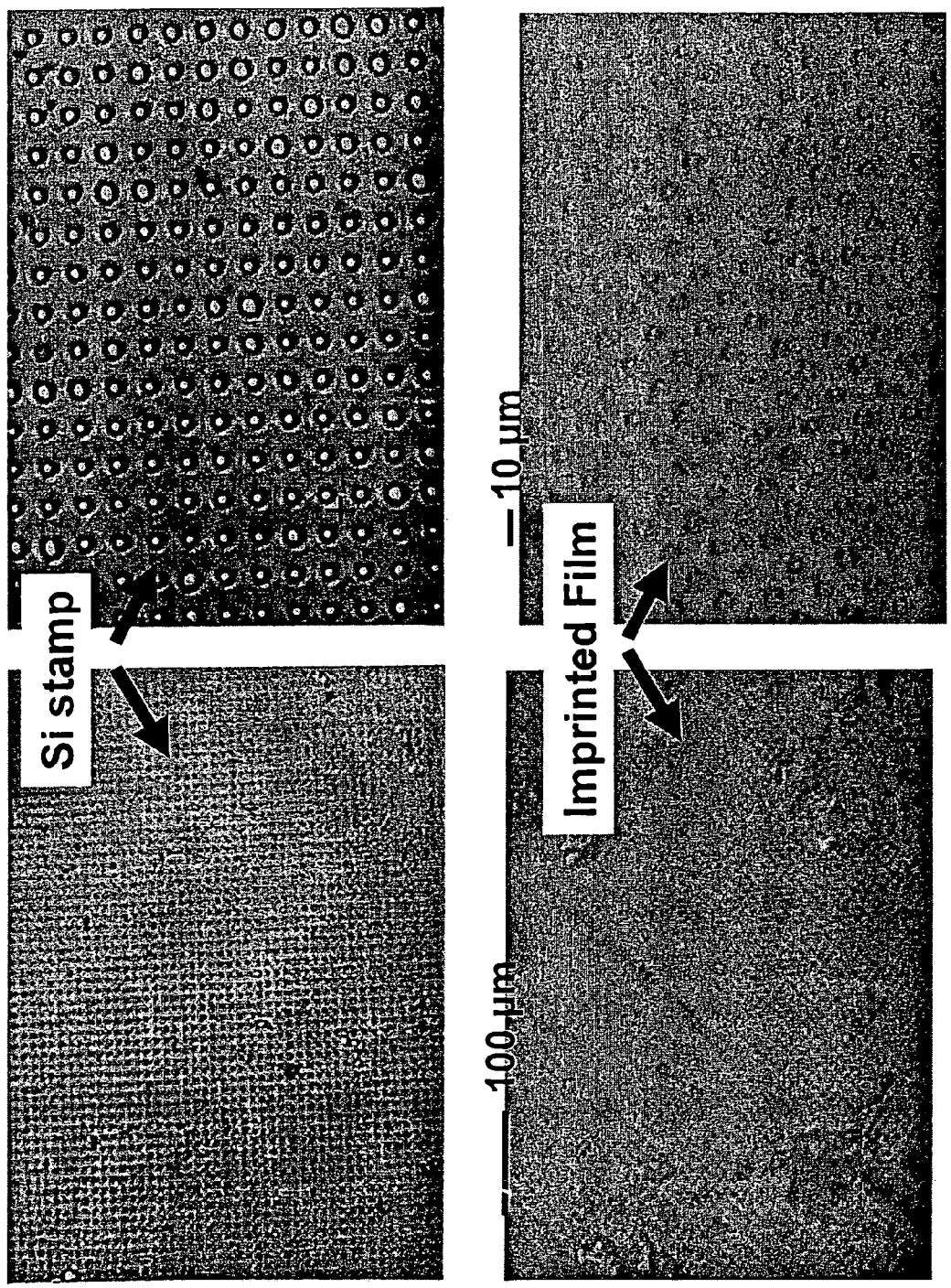
FIG. 8 shows optical images comparing the original micron-scale stamp with the imprinted surface of the tablet film coating.

FIG. 7 is taken from a working example described further below. It shows AFM images of micropatterns on a pharmaceutical film coating for a pharmaceutical drug. FIG. 8 is also taken from a working example which further shows optical images.

Figure 11:
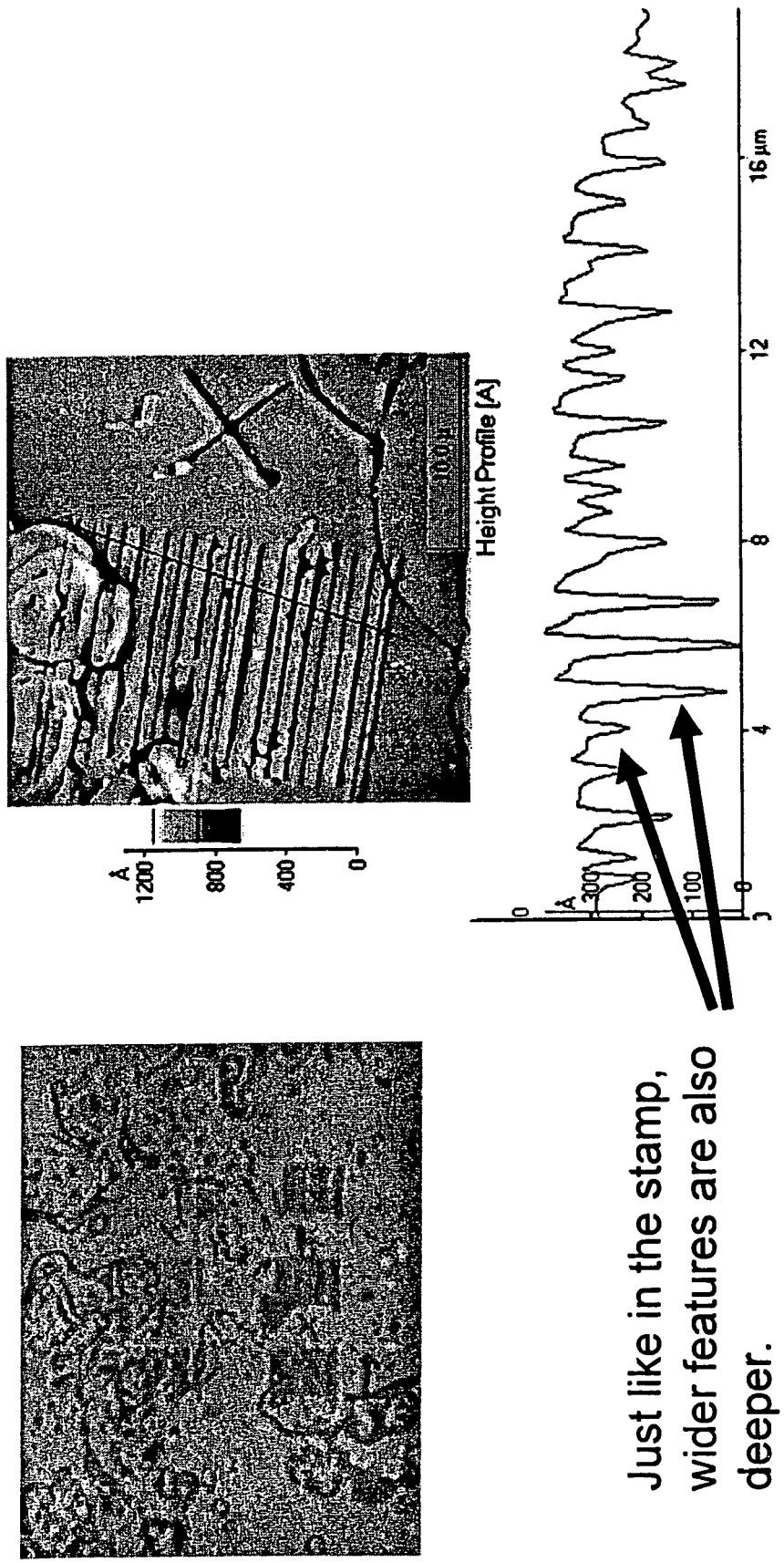
FIG. 11 shows an optical image and an AFM image of a stamped pill surface.

FIG. 11 is a working example and shows identification features which are nanopatterns imprinted onto a pharmaceutical film coating.

The pharmaceutical compositions, their properties, and endurance over time and use, can be further tested by use of known ASTM tests such as, for example, D4169; D5276; D642; D4169; D999; D4729. These are important for examining the impact of distribution. For example, these methods can be used to test for compression and thermal properties. Drop testing, manual handling, compression testing, repetitive shock, loose load vibration, random vibration, vehicle vibration, and other testing can be examined.

II. Methods of Making the Pharmaceutical Composition

Another embodiment of the invention is making pharmaceutical compositions which have at least one identification region and at least one identification feature. For example, the invention provides a method of making a pharmaceutical composition having at least one identification region and at least one identification feature comprising: (i) providing a stamp which has a surface to form at least one identification region having at least one identification feature; (ii) providing a pharmaceutical composition having a surface; and (iii) contacting the stamp and the pharmaceutical composition under conditions so that the pharmaceutical composition comprises a surface having the at least one identification region having at least one identification feature. The stamp can be removed from the pharmaceutical composition under conditions so that the image of the stamp is transferred to be an image on the pharmaceutical composition in sufficiently high quality to be useful in commerce. The surface of the stamp and the surface of the pharmaceutical composition of course are related in that images on each are spatially in a positive-negative relationship. In other words, a positive image on a stamp provides a negative image on a stamped surface, and a negative image on a stamp provides a positive image on a stamped surface. In conducting the contacting step, the stamp and pharmaceutical composition move relative to each other. One of the two can be held stationary while the other one moves to initiate contact. For example, the stamp can be held stationary or the pharmaceutical composition can be held stationary.

Taken from a working example described further below, FIG. 8 illustrates, for example, the ability to compare the image of the stamp with the image of the material stamped.

Conditions for stamping can be varied depending on the pharmaceutical composition and the results desired. The proper tradeoff between quality of stamping and production rate can be achieved. For example, the time of stamping can be varied; the pressure of stamping can be varied; the surface treatment of the contacting surfaces can be varied; the instrument used for stamping can be varied. The stamping time is not particularly limited but can be, for example, about 0.001 seconds to about 50 seconds, about 0.01 seconds to about 50 seconds, about 0.1 seconds to about 50 seconds, or about 0.5 seconds to about 25 seconds, or about 1 second to about 10 seconds. The stamping temperature can be, for example, about 25° C. to about 400° C., or about 50° C. to about 300° C., or about 100° C. to about 250° C. Heat used to vary temperature can be supplied through the stamp, through the pharmaceutical composition, or through the surrounding medium such as air. Generally, temperature is selected to avoid degrading any of the composition or cosmetically interfering such as discoloring the composition. Stamping force and pressure is not particularly limited but can be adjusted together with the stamp time and temperature to give the best balance of quality and production rate. Examples of stamping pressure include, for example about 0.01 MPa to about 1,000 MPa, and more particularly, about 0.1 MPa to about 100 MPa, and more particularly, about one MPa to about 15 MPa.

Other known stamping and molding methods can be adapted and used. For example, release coatings are known in the molding arts and can be used including for example hydrophobic release coatings. Hydrophobic materials can be used to form the stamp or surface coat the stamp, including monolayers such as self-assembled monolayers including reactive silane compounds. Trichloro/trialkoxysilane-based self-assembled monolayer coatings can be useful, for example.

Stamps can be used repeatedly such as, for example, at least one hundred times, at least 1,000 times, or at least 10,000 times. Anti-fouling methods can be carried out to prevent undesirable material from building up on the stamp over time and with use. For example, coatings can be put on the stamp to improve anti-fouling and durability. Use of hard coatings including diamond like coatings (DLC) can be utilized, for example.

An important advantage of the present invention is that (1) it does not generally require the deposition of a film prior to stamping; (2) upon formation of the image, addition post-processing and etching is generally not needed, and (3) the method can be applied to curved and other non-flat surfaces. For example, by contrast, nanoimprint lithography (NIL) is a method which generally involves the fabrication of microchips on a wafer including (a) deposition of a thin, polymer film and (b) subsequent processing, including etching, after the image is formed and transferred from a stamp to a surface. See, for example, Chou et al. Applied Physics Letters 67(21), 1995. More recent examples of imprint nanolithography technical literature also includes U.S. Pat. Nos. 6,656,398; 6,696,220; and 6,719,915 (Step and Flash Imprint Lithography). A basic and novel feature of the present invention is that these additional processing steps, in particular additional etching steps, can be eliminated. Hence, the invention can provide, for example, a method of making a pharmaceutical composition having at least one identification region and at least one identification feature consisting essentially of: (i) providing a stamp which has a surface to form at least one identification region having at least one identification feature; (ii) providing a pharmaceutical composition having a surface; and (iii) contacting the stamp and the pharmaceutical composition under conditions so that the pharmaceutical composition comprises a surface having the at least one identification region having at least one identification feature. Additional etching is not needed.

III. Other Objects and Compositions with Identification Features

As described in Sections I and II, a particular preferred example of the invention is a pharmaceutical composition, and methods of making the pharmaceutical composition. In general, the various embodiments of the invention can be applied to pharmaceutical goods which are susceptible to counterfeiting, including for example high priced pharmaceuticals, prescription drugs, and blockbuster drugs with large sales volume, wherein price differentials exist from country to country and the economic incentive to counterfeit is high, as described above. The description above for pharmaceutical compositions, and methods of making, generally can be also adapted to apply to other compositions and objects which can be subjected to counterfeiting fraud such as the confectionary compositions and consumer goods like CDs or DVDs.

Hence, the invention also relates to objects and compositions which have a surface, wherein the surface comprises at least one identification region having at least one identification feature. The surface, identification region, and the identification feature are described further above in Section I. An object broadly can be a variety of items including items of commerce and is not particularly limited by any shape or form. It can be man-made or natural. Typically, an object can have a particular use or function and can comprise one or many compositions. A composition also broadly can be a variety of materials, chemical compounds, elements, mixtures, blends, composites, metals, glasses, polymers, ceramics, and the like and is not limited by a particular use or function. The identification feature on the object or composition can have relatively small lateral and vertical dimensions. The feature can be a positive feature, protruding from the surface, or a negative feature, extending into the surface.

One embodiment, for example, comprises an object comprising: an object having a surface, wherein the surface comprises at least one identification region having at least one identification feature which has a lateral dimension of about 500 microns or less.

Another embodiment is for a composition comprising: a composition having a surface, wherein the surface comprises at least one identification region having at least one identification feature which has a lateral dimension of about 500 microns or less.

Preferred examples of objects include currency, consumer products, paper, money, documents, entertainment media, compact disks, DVDs, nickel masters, flat wafers, disk drive heads, semiconductor chips, integrated circuits and their components, packaging containers and materials including packaging containers and materials for pharmaceuticals, jewelry, precious raw materials, personal and institutional identification devices, medical devices, bottle tampering-evident seals, syringes, jewelry and collectibles. In particular, syringes, pre-loaded syringes, vaccines and vaccine vials, and injectable drug vials, including bottle seal, medical devices including catheters and implantable devices, and packaging labels can be used. In general, objects which are susceptible to counterfeiting or copying are particularly of use.

Preferred examples of compositions include pharmaceutical, medications, drugs, food, and confectionary.

In general, the composition can be a material which can be imprinted. They can be, for example, thermoplastic materials which can soften with heat and then become hard at lower temperatures. Thermosetting or crosslinking compositions can be also used wherein the material is in a soft form and then subjected to imprinting. Curing or hardening steps can be then carried out to lock in the imprinting.

The invention also relates to methods of making the objects and the compositions by methods analogous to those described in Section II.

If desired, a material can be provided with the at least one identification region having at least one identification feature, and then the material can be combined with an API.

IV. The Stamp

The pharmaceutical compositions, as well as other objects and compositions, can be made with one or more stamps which provide the surface with the identification feature. The invention provides a stamp for use in making a pharmaceutical composition, or other objects and compositions, the stamp comprising a surface having at least one identification region, and the region having at least one identification feature. In general, the stamps can be master stamps and can be used repeatedly, or can be used to produce other stamps.

Because the stamp can have a shape which is transferred to the pharmaceutical composition, or other objects and compositions, the dimensions described herein for the identification features and identification regions can also be used to describe the stamp. For example, a stamp which has an identification feature having a 100 nm height can result in a pharmaceutical composition, or other composition or object, having an identification feature with 100 nm height. The stamp's 100 nm positive protrusion can produce a 100 nm negative inversion.

In particular, the identification regions and features on the stamp can be characterized by dimensional measurements such as lateral dimensions or vertical dimensions with respect to the surface. Conventional methods can be used to measure these dimensions including methods described herein and the working examples. Conventional data processing including image processing, pattern recognition, curve fitting and optical character recognition (OCR) can be carried out to provide dimensions and average dimensions and generally to provide useful data.

The identification regions of the stamp can each have one or more identification features which can be characterized by a lateral dimension with respect to the surface. The lateral dimension can be, for example, a width or a length such as, for example, a circle diameter or a line width, or the relative or absolute position compared to a known mark. The lateral dimension is different from a vertical dimension such as height. For an identification feature which is a line, the lateral dimension of length can be sufficiently long that it can be viewed with the naked eye or an optical microscope, whereas the lateral dimension which is width can be sufficiently small that it cannot be seen with a naked eye or optical microscope. The size of the lateral dimensions can be sufficiently small so that the identification features are invisible to the naked eye and difficult to detect by conventional, simple methods. Rather, difficult, relatively expensive methods can be used to detect small identification features including microscopic and nanoscopic features. At least one of the lateral dimensions can be made small. For example, the identification feature of the stamp can have a lateral dimension of, for example, about 500 microns or less, or about 400 microns or less, or about 300 microns or less, or more particularly, about 250 microns or less, or more particularly, about 100 microns or less, or more particularly, about 10 microns or less. Or the identification feature can have a lateral dimension of, for example, about one micron or less, or more particularly, about 500 nm or less, or more particularly, about 250 nm or less, or more particularly, about 100 nm or less. There is no particular limit to how small the lateral dimension can be as long as the identification feature can be detected. For example, the lateral dimension can be at least about 1 nm, or more particularly, at least about 10 nm, or more particularly, at least about 100 nm, or more particularly at least about one micron. Hence, exemplary ranges for the lateral dimension include about one nm to about 500 microns, about 10 nm to about 100 nm, about 100 nm to about one micron, and about one micron to about 500 microns.

For barcodes on the stamp, the line length is not particularly limited but can vary from nanoscopic to microscopic. For example, lines can be about one micron to about 50 microns long, or about 5 microns to about 25 microns long, and yet have a line width of only about 50 nm to about 150 nm wide.

The identification features on the stamp can be in the form of a pattern of repeating features such as dots or lines, wherein the features are characterized by an average lateral dimension such as average circle diameter or line width. The lateral size dimensions described herein can be computed into average lateral dimensions.

The identification features on the stamp can have a vertical dimension such as a height dimension or a depth dimension, and these terms are used interchangeably and for both positive structures and negative structures. The height dimension is not particularly limited and can be, for example, about one micron or less, or more particularly, about 500 nm or less, or more particularly about 250 nm or less, or more particularly about 150 nm or less. There is no particular lower limit to the height dimension as long as the identification feature can be detected. The height dimension can be, for example, about one nm or more, or about 10 nm or more, or about 25 nm or more. Exemplary ranges can be, for example, about one nm to about one micron, or about 10 nm to about 500 nm, or about 25 nm to about 250 nm. Again, if a pattern of repeating identification features are used, the vertical dimension can represent an average dimension.

In addition to the lateral dimension and the height dimension for identification features on the stamp, the invention can be also characterized by a separation dimension which represents the distance between the identification features such as a separation distance or a pitch. In other words, the one or more identification features can be separated from each other by a particular distance, and this distance can be an average distance for an array of identification features. For example, if the identification features are a series of lines, a distance can be measured between the centers of the lines, or if the identification features are a series of dots, a distance can be measured between the centers of the dots. The distance of separation is not particularly limited but smaller separation distances are preferred so that the identification is invisible to the unaided eye. For example, the one or more identification features can be separated from each other by an average distance of about 500 microns or less, or more particularly, about 100 microns or less, or more particularly, about 10 microns or less, or more particularly, about one micron or less, or more particularly, about 500 nm or less.

The stamp can also be characterized by the density of the identification features. For example, a plurality of parallel lines can be generated wherein there is at least one line per every two microns, or at least one line per every one micron, or at least one line per every 0.5 microns. See for example FIG. 1, wherein a height profile scan be used to determine a density.

The information associated with the identification region and features may be obtained by determining one or more of the aforementioned characteristics and optionally a mathematical function or algorithm.

The surface of the stamp also can comprise one or more marks which can be detected by an optical microscope or an unaided eye. The at least one mark can be located outside of the identification region. Examples include an X shaped mark. The marks, for example, can have lateral dimensions such as line width at the micron scale such as 10 microns or more, at least 50 microns or more, at least 100 microns or more.

The stamp can also comprise the identification regions described above for the pharmaceutical composition. The identification region can be characterized by an identification region area which has an enclosing perimeter around the identification features so that all of the identification features can be found within the enclosing perimeter. This area can be for example, about 10,000 square microns or less, or about 1,000 square microns or less, or about 400 square microns or less, or about 4 square microns or less, or about one square micron or less. The identification region can be, for example a square region with a lateral length and width of 100 microns×100 microns, respectively, or 20 microns×20 microns, or 2 microns×2 microns. Or the identification region can be, for example, a generally rectangular region or circular region. In many cases, two or more identification regions are desired in case one or more of the identification regions become unreadable by scratching, rubbing, or some other undesirable event. For example, the surface of the stamp can comprise more than 20, more than 30, more than 40, or more than 50 identification regions. The identification region can be sufficiently large to be seen by the naked eye or an optical microscope, even when identification features within the identification region can be sufficiently small that they cannot be seen by the naked eye or even with an optical microscope.

The material of the stamp is not particularly limited. In general, the stamp can have a surface which is made of a harder or stiffer material than the material of the surface to be stamped. Materials that can provide high aspect ratio structures can be used. For example, materials can be used which can be subjected to etching processes which result in high aspect ratios such as, for example, reactive ion etching. Stamp material can be, for example, silicon, silicon oxide, quartz, and nickel, and other substrates popular for semiconductor processing.

Stamps can be also treated to increase the durability of the stamp. For example, stamp surfaces can be coated with diamond like coatings (DLC), or nickel films to increase hardness and decrease wear. Stamps fabricated from silicon substrates can be oxidized to increase the hardness of the stamp surface.

A master stamp can be used to produce daughter stamps which are substantially identical but inverted copies of the master.

In another embodiment, indirect nanolithography can be used to selectively remove or modify areas in a resist film coating a substrate. The patterned substrate can be subjected to etching to generate negative relief features, such as trenches, in the substrate. Stamps with negative relief features will result in positive features when used for printing. Negative relief stamps can be replicated to generate secondary stamps that have positive features.

Figure 2:
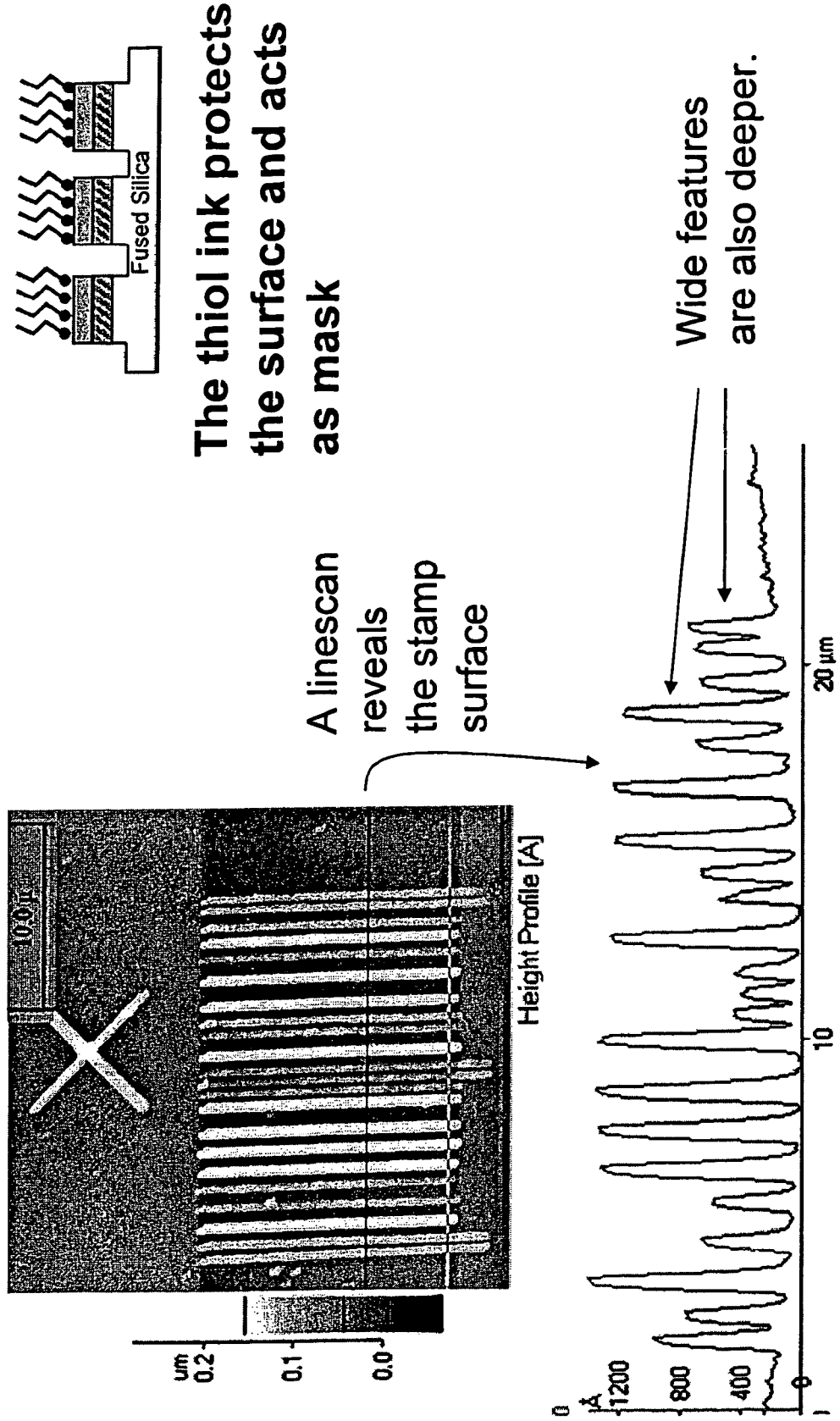
FIG. 2 shows AFM scan of a silicon master stamp with a height line scan (after etching).

FIG. 2 is a working example described further below. It provides an AFM scan of a stamp which has an identification region and identification features which can be transferred to the object, composition, and pharmaceutical composition. For example, it comprises at least six identification features and in particular at least nine identification features. The positive features rising out of the surface have a generally triangular shape according to the height profile analysis. The scan shows nine lines in approximately parallel arrangement. The center of the line can be used to measure a separation distance.

FIG. 6 is another working example further described below. Here, a pattern of dots are used. The density of dots in the cross-sectional height profile is better than one dot per 10 microns. FIG. 1 is a working example and shows SEM scans of several stamps. FIG. 3 is a working example and shows a plurality of identification regions on one stamp. Each identification region comprises a series of identification features which are barcode lines.

In the nanolithography regime, nanoimprint lithography is a method which can be used in some cases to generate features having lateral dimensions below 200 nm using a stamp on polymer-coated semiconductor wafer. See, for example, U.S. Pat. Nos. 5,772,905 to Chou ("Nanoimprint Lithography"); 6,309,580 to Chou; 6,482,742 to Chou; and 6,518,189 to Chou. The method employs use of stamps having protruding features and made of stiff materials. These references can be used to practice the invention both with respect to the final stamp and the methods of making and using the stamp. Commercial products including stamping instruments and molds or masks are available from Nanonex Corp. (Princeton, N.J.), Suss Microtech AG (Munich, Germany); EV Group (Schareding, Austria); Molecular Imprints Inc (Austin, Tex.); and Obducat (Malmo, Sweden).

Generally, stamp materials which can be used in NIL can be used in this invention. If silicon materials are used, they can be oxidized to silicon dioxide to improve properties such as, for example, durability.

V. Method of Making the Stamp

A variety of methods can be used to make the stamp. These methods can be carried out with use of microlithography or nanolithography and can provide excellent high resolution identification features. For example, DPN printing, nanoimprint lithography, microcontact printing, electron beam lithography, ion beam lithography, laser-based lithography, optical lithography, nanografting, and the like can be used.

For example, in one embodiment, the invention provides a method for making a stamp comprising the steps of (i) writing a pattern with a resist material by nanolithography or microlithography on a substrate, (ii) etching the patterned substrate, and optionally (iii) further treating the patterned and etched substrate to form the stamp. For example treatment step (iii) can comprise removing the resist, or any other layers which are undesired in the final stamp.

In one embodiment, direct write nanolithography can be used to pattern a monolayer resist on a substrate. The patterned substrate can be subjected to etching including wet etching or dry etching to remove areas unprotected by the resist. Finally, the resist itself can be removed. The resist can be, for example, a compound which covalently bonds or chemisorbs to the substrate. The resist can be, for example, an alkanethiol on a gold substrate. The substrate can be, for example, fused silica having an outer layer of metal with an intermediate adhesion layer as needed. The direct write nanolithographic method can be carried out with use of a nanoscopic tip to transfer resist material to the substrate by deposition.

Figure 4:
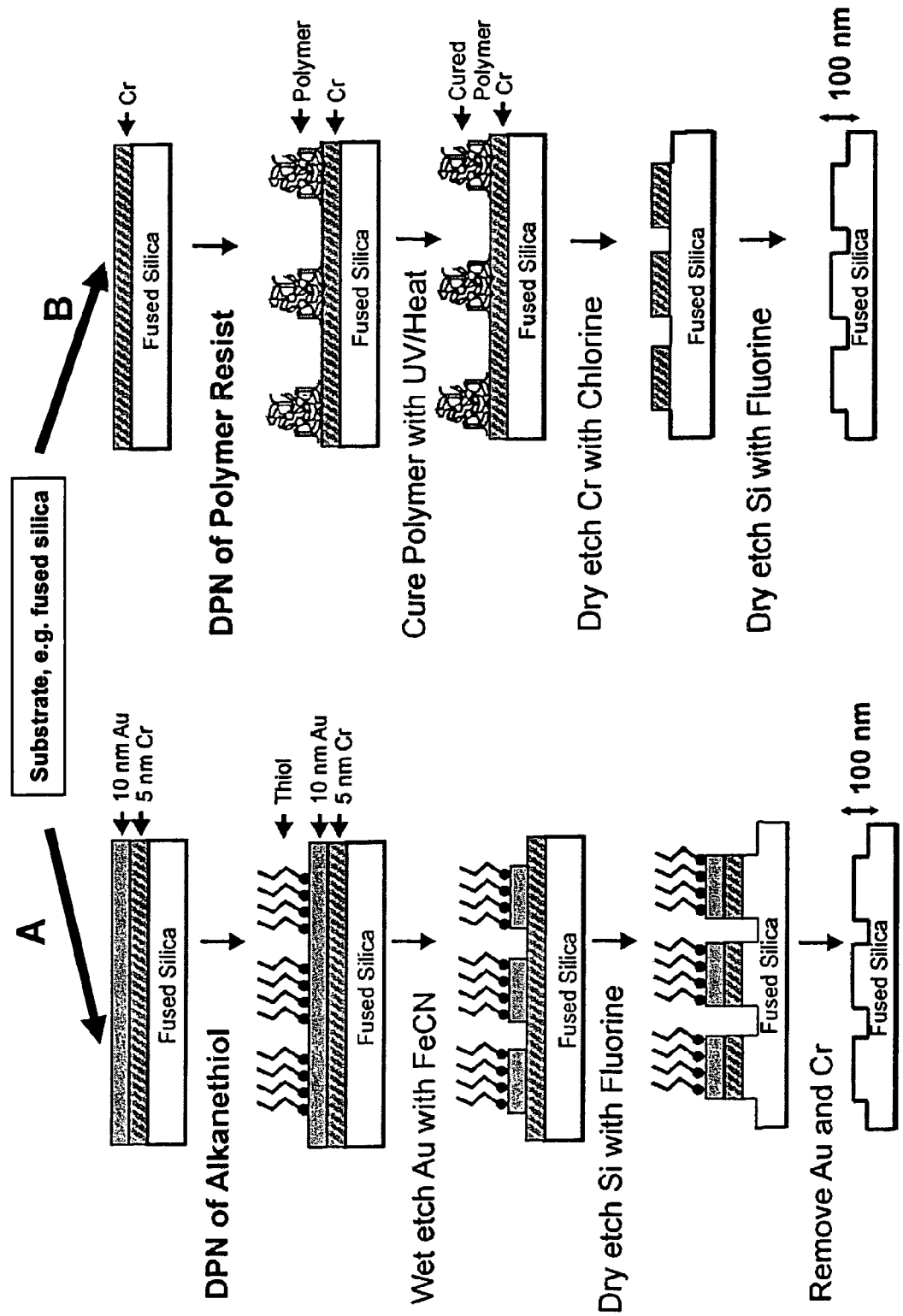
FIG. 4 shows a general fabrication process for patterning and etching to generate a high resolution stamp.

In another embodiment, illustrated in FIG. 4, direct write nanolithography can be used to pattern a resist on a substrate. The resist can be a curable material such as, for example, a UV curable or heat curable polymer. Etching can be carried out and the resist removed.

Figure 5:
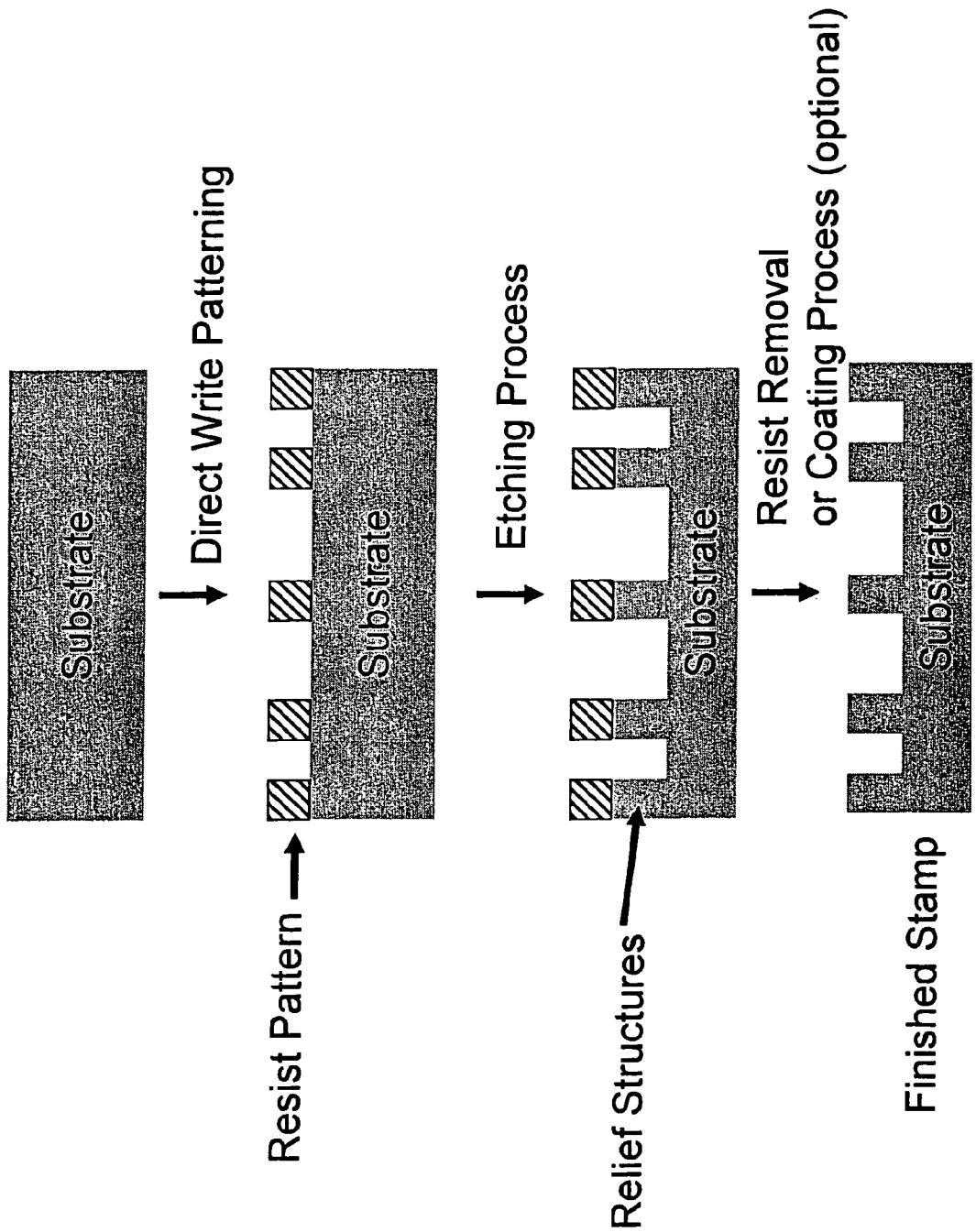
FIG. 5 shows two stamp fabrication processes for high resolution which use DPN printing and etching.

FIGS. 5A and 5B further illustrate embodiments for stamp fabrication. Two process pathways are illustrated which each begin with a fused silica substrate and end with a fused silica stamp. These processes can be used also to make stamps in silicon substrates.

In the left pathway (FIG. 5A), a thermally oxidized silicon or fused silica substrate is provided which comprises further a gold surface layer and an interfacial adhesion layer of chromium. DPN printing can be carried out to produce a pattern of an alkanethiol on the gold surface. Wet etching can be carried out to etch away the gold layer not protected by the resist. Dry etching can be carried out to further remove chromium and silica. Finally, the resist, gold, and chromium can be further removed to yield the stamp.

In the right pathway (FIG. 5B), a fused silica substrate is provided which further comprises a chromium surface layer. DPN printing can be carried out to produce a pattern of a polymer resist on the chromium. The polymer can be cured by heat or light. After curing, dry etching by, for example, chlorine can be carried out to remove chromium. Finally, the resist, chromium, and silica can be removed to yield the stamp.

A stamp made by the methods disclosed above can be replicated into secondary stamps, as many identical stamps may be required for commercial production. Furthermore, the identification features present on the master stamp may be replicated multiple times on a secondary stamp, providing redundancy as discussed above. The master stamp may be replicated e.g. by stamping, molding into a soft material (or other methods known to the art), followed by a hardening or coating step, for example polymeric curing, vacuum physical vapor deposition, electroless plating, electroplating or a combination thereof.

In another embodiment, the stamp is replicated on a thin film or foil which is wrapped around a cylinder, then hardened or coated by a hard material. Alternatively, a cylinder may be rolled over the stamp, duplicating the stamp features on said cylinder. See the related art in Chou et al. *JVST B*16(6), 1998. The cylinder is then used as a stamp by rolling it over the desired pharmaceutical composition or object.

The processes are further described in the working examples.

VI. Direct-Write Nanolithography and DPN Printing in Making the Stamp

In a preferred method, direct-write nanolithography is used in the process to prepare the stamp. A preferred method is the use of deposition of inks or patterning compounds from a fine, sharp needle like structure which can be, for example, a scanning probe cantilever with or without a tip. The needle like structure can have the patterning compound at the end and can be used to deposit the ink or patterning compound to a substrate. A preferred method of direct-write nanolithography is DPN printing. This method provides for exceptionally high resolution and good patterning capability.

For example, DPN printing technology and etching procedures are described in pending patent application to Mirkin et al. "Fabrication of Solid-State Nanostructures including sub-50 nm Solid-State Nanostructures Based on Nanolithography and Chemical Etching" filed Dec. 3, 2003 (Ser. No. 10/725,939), which is hereby incorporated by reference in its entirety. This application also describes a series of geometric patterns which can be used for the identification features.

In addition, DPN™ printing and deposition methods are extensively described in the following patent applications and patent publications, which are hereby incorporated by reference in their entirety and support the disclosure for the present inventions, particularly with respect to the experimental parameters for carrying out the deposition:

1. U.S. Provisional application 60/115,133 filed Jan. 7, 1999 ("Dip Pen Nanolithography"). This describes applications of deposited monolayers as etch resists.

2. U.S. Provisional application 60/157,633 filed Oct. 4, 1999 ("Methods Utilizing Scanning Probe Microscope Tips and Products Therefor or Produced Thereby").

3. U.S. Regular patent application Ser. No. 09/477,997 filed Jan. 5, 2000 ("Methods Utilizing Scanning Probe Microscope Tips and Products Therefor or Produced Thereby"), now U.S. Pat. No. 6,635,311 to Mirkin et al. issued Oct. 21, 2003. A wide variety of inks and substrates are described which show chemisorption between the ink and the substrate and can be used as an etch resist.

4. U.S. Provisional application 60/207,713 filed May 26, 2000 ("Methods Utilizing Scanning Probe Microscope Tips and Products Therefor or Produced Thereby"). This application, for example, describes wet chemical etching, working examples, references, and figures, which are all incorporated by reference in their entirety.

5. U.S. Provisional application 60/207,711 filed May 26, 2000 ("Methods Utilizing Scanning Probe Microscope Tips and Products Therefor or Produced Thereby").

6. U.S. Regular application Ser. No. 09/866,533 filed May 24, 2001 ("Methods Utilizing Scanning Probe Microscope Tips and Products Therefor or Produced Thereby"). This application, for example, describes wet chemical etching, working examples (e.g., example 5), references, and figures, which are all incorporated by reference in their entirety. Computer control of the nanolithographic deposition is also described.

7. U.S. patent publication number 2002/0063212 A1 published May 30, 2002 ("Methods Utilizing Scanning Probe Microscope Tips and Products Therefor or Produced Thereby").

8. U.S. patent publication number 2002/0122873 A1 published Sep. 5, 2002 ("Nanolithography Methods and Products Produced Therefor and Produced Thereby").

9. PCT publication number WO 00/41213 A1 published Jul. 13, 2000 based on PCT application no. PCT/US00/00319 filed Jan. 7, 2000 ("Methods Utilizing Scanning Probe Microscope Tips and Products Therefor or Produced Thereby").

10. PCT publication number WO 01/91855 A1 published Dec. 6, 2001 based on PCT application no. PCT/US01/17067 filed May 25, 2001 ("Methods Utilizing Scanning Probe Microscope Tips and Products Therefor or Produced Thereby").

11. U.S. Provisional application 60/326,767 filed Oct. 2, 2001, ("Protein Arrays with Nanoscopic Features Generated by Dip-Pen Nanolithography"), now published 2003/0068446 on Apr. 10, 2003 to Mirkin et al.

12. U.S. Provisional application 60/337,598 filed Nov. 30, 2001, ("Patterning of Nucleic Acids by Dip-Pen Nanolithography") and U.S. regular application Ser. No. 10/307,515 filed. Dec. 2, 2002 to Mirkin et al.

13. U.S. Provisional application 60/341,614 filed Dec. 17, 2001, ("Patterning of Solid State Features by Dip-Pen Nanolithography"), now published 2003/0162004 Aug. 28, 2003 to Mirkin et al.

14. U.S. Provisional application 60/367,514 filed Mar. 27, 2002, and publication no. 2003/0185967 on Oct. 2, 2003 to Eby et al. This patent application describes computer control of nanolithographic procedures.

15. U.S. Provisional application 60/379,755 filed May 14, 2002, ("Nanolithographic Calibration Methods") and U.S. regular application Ser. No. 10/375,060 filed .Feb. 28, 2003 to Cruchon-Dupeyrat et al. This patent application describes computer control of nanolithographic calibration procedures.

16. U.S. patent application Ser. No. 10/689,547 filed Oct. 21, 2003 to Crocker et al. ("Nanometer-Scale Engineered Structures, Methods, and Apparatus for Fabrication Thereof, and Application to Mask Repair, Enhancement and Fabrication"). This describes for example use of nanolithography to make photomasks and nanoimprint lithography stamps.

17. U.S. patent application Ser. No. 10/705,776 filed Nov. 12, 2003 to Cruchon-Dupeyrat ("Methods and Apparatus for Ink Delivery to Nanolithographic Probe Systems"). This describes, for example, use of reactive ion etching to make deep structures.

18. U.S. Provisional application 60/544,260 filed Feb. 13, 2004 ("Direct-Write Nanolithography with Stamp Tip: Fabrication and Applications"). This describes, for example, elastomer modification of tips.

19. U.S. Provisional application 60/547,091 filed Feb. 25, 2004 ("Methods for Patterning Conductive Material."). This describes, for example, use of tipless cantilevers.

In general, state of the art DPN™ printing and deposition-related products, including hardware, software, and instrumentation are also available from NanoInk, Inc. (Chicago, Ill.), and these can be used to carry out the present invention. For example, commercially available products include NSCRIPTOR, DPN-System-1, environmental chamber, probes, pens, inkwells, substrates, substrate holders, and various accessories including ink dispensing kits, ink dispersion syringes, replacement needles, and probe clips. NSCRIPTOR features for example InkCAD system control, closed loop scanning, and a series of computer programs to facilitate automation. Calibration can be carried out with InkCal. Probes can be single probes, passive multiple probe arrays, active probes, or probes for AC mode.

Parallel methods of the DPN printing process in active mode can be carried out as described in, for example, U.S. Pat. No. 6,642,129 to Liu et al. issued Nov. 4, 2003.

In addition, the following papers describes wet chemical etching procedures used in conjunction with direct-write nanolithography, and is hereby incorporated by reference in its entirety including figures, references, and working examples: Zhang et al., "Dip-Pen Nanolithography-Based Methodology for Preparing Arrays of Nanostructures Functionalized with Oligonucleotides"; *Adv. Mat.*, 2002, 14, No. 20, October 16, pages 1472-1474; Zhang et al., "Biofunctionalized Nanoarrays of Inorganic Structures Prepared by Dip-Pen Nanolithography"; *Nanotechnology*, 2003, 14, 1113-1117 (see further parts V and VI below).

Figure 9:
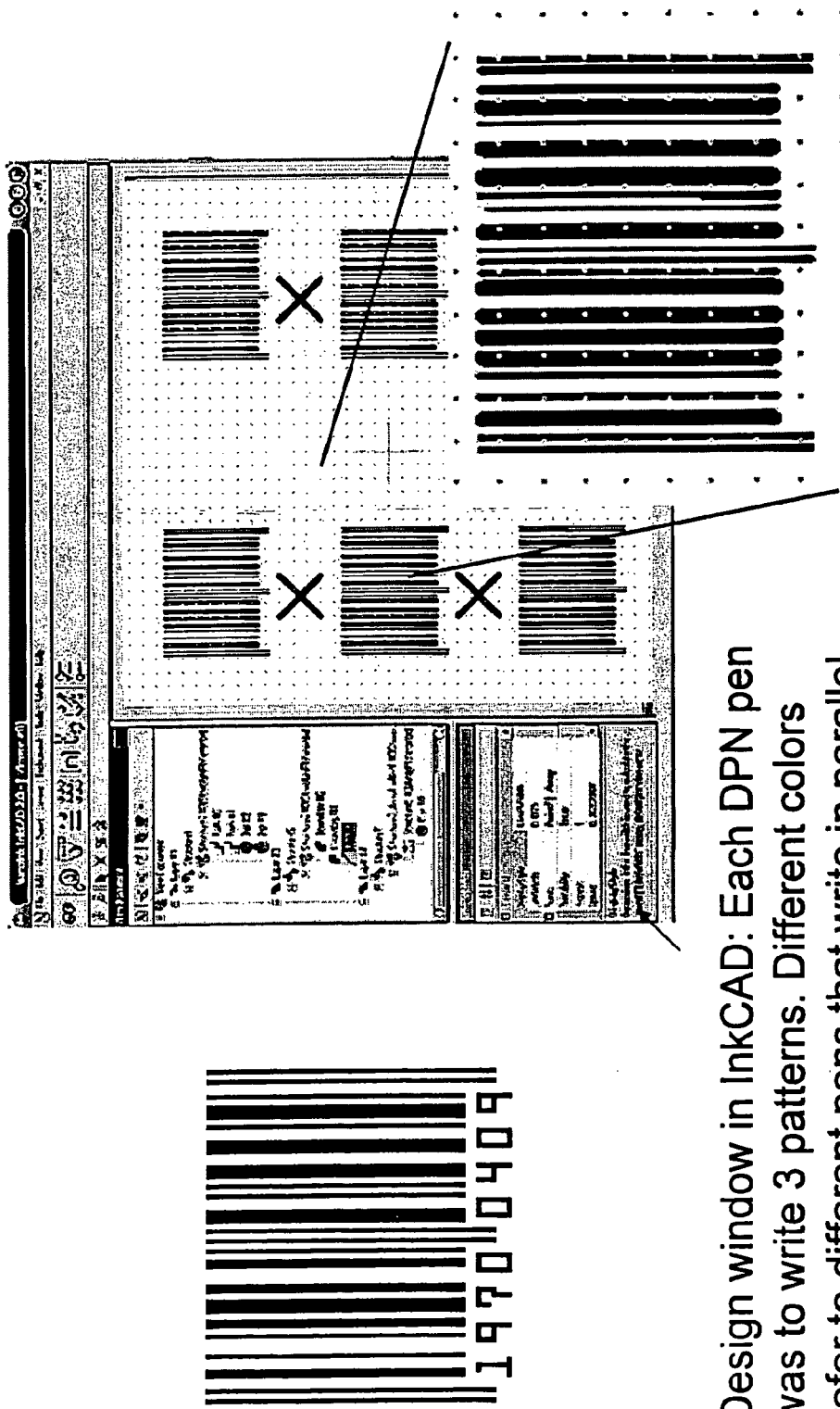
FIG. 9 shows how the NSCRIPTOR instrument is used for designing barcode patterns.

FIG. 9 illustrates use of NanoInk's NSCRIPTOR DPN-Writer in designing and writing patterns. Using computer generated images, which can be translated into physical patterns on surfaces, a wide variety of useful identification features and regions can be generated.

VII. Use of Lithography in Identification Processes

The invention provides the use of lithography, including microlithography and nanolithography, in the identification of objects and compositions which are subject to counterfeiting including pharmaceutical compositions. The lithography can be indirectly used to prepare stamps, and then the stamps can be used to provide the identification features on the objects and compositions. Alternatively, the lithography can be used to directly write the identification features on the objects and compositions. Direct-write methods of lithography are preferred including the methods described above in Section VI and references cited therein. Methods which comprise use of deposition of material from a scanning probe microscopic tip can be used including AFM methods. Methods involving cantilevers can be used including both tip and tipless cantilevers.

VIII. The Stamping Instrument

In general, stamping instruments and components for stamping such as stamps are commercially available. They range from automatic production machines to manual research machines, and they can be adapted as needed to accommodate the stamps described herein. Other terms used in the art for stamping instruments including stamping machines, imprinting machines, marking machines, presses, and the like. Instruments are particularly of use when they are adapted to process pharmaceutical compositions and be in compliance with federal regulations for pharmaceuticals. The instrument generally comprises mechanical and electrical components which continuously and automatically deliver an object such as a pill or a tablet for stamping to a stamping site. The instrument also generally comprises mechanical and electrical components which provide for stamping of the object at the stamping site. The instrument further comprises mechanical and electrical components which continuously and automatically transport the object away from the stamping site after stamping. As known in the art, conveyor systems can be used to transport the objects in a continuous, high-speed, manufacturing operation. The instruments also can comprise components which provide for printing, sorting, inspecting, and feeding. The stamping methods generally can be coupled with other methods used to process pharmaceutical compositions.

Some examples from the technical literature are noted, and the complete disclosures of these following patents are incorporated herein by reference in their entirety for their description of instrumentation for processing of compositions including pharmaceutical compositions.

For example, U.S. Pat. Nos. 5,023,437 and 4,591,279 to Speicher et al. are incorporated and describe marking the surface of objects with bar codes, including a marking machine. U.S. Pat. No. 4,574,694 is incorporated and also describes a stamping machine.

U.S. Pat. No. 4,189,996 to Ackley et al. is incorporated and describes an apparatus adapted to transport and imprint indicia around the circumference of generally cylindrical objects such as capsules. See also U.S. Pat. No. 3,272,118 to Ackley et al which is incorporated. Additional patents assigned to Ackley include U.S. Pat. Nos. 5,630,499; 5,878,658; 6,286, 421; 6,314,876; 6,450,089; and 6,481,347, which are incorporated.

U.S. Pat. No. 5,376,771 to Roy is incorporated and describes a high speed process for digital laser marking of pharmaceutical compositions including an instrument in FIG. 1.

Stamping instruments and components including tablet presses including rotary tablet presses are available from a variety of companies including, for example, Ackley Machine Corp. (Moorestown, N.J.); R. W. Hartnett Co. (Philadelphia, Pa.); CapPlus Technologies (CPT); and Fette Compacting America (Rockaway, N.J. & Schwarzenbek, Germany).

In addition, see, e.g., stamping instruments and components from companies marketing NIL including Suss Microtech AG (Garching/Munich Germany); EV Group (Schareding, Austria); Nanoex Corp. (Princeton, N.J.); Molecular Imprints (Austin, Tex.); and Obducat (Malmo, Sweden).

For an automated stamping instrument, the production rate for stamping can be controlled to provide the best balance of quality and speed. The production rate for stamping can be, for example, at least 1,000 units per hour, or at least 10,000 units per hour, or at least 100,000 units per hour, or at least 1,000,000 units per hour.

A stamping instrument was constructed and used to carry out the working examples described below and is further illustrated in FIGS. 13-16. This instrument can be adapted to provide continuous operation under automated conditions with computer control.

The stamping instrument can comprise (i) a device which is adapted to be coupled to a stamp; (ii) a mount which is adapted for holding an object or composition, wherein the device and the mount are operably connected to provide relative motion and stamping of the object or composition by the stamp.

A stamp can be coupled to the device and uncoupled from the device, and replaced as desired with a different stamp. Hence, a stamp can comprise not only a surface having the image to be stamped but also, if desired, coupling features which allow coupling of the stamp to the device.

A support structure can be used to operably connect the device and the mount and assist in providing the relative motion and stamping. For example, the support structure can comprise a ram bearing and a pressure ram. The support structure can include an operably connected pressure ram which can move in relation to the support structure through, for example, a ram bearing and provide motion of the stamp relative to the mount. The support structure can also comprise a heater, for controlling temperature of the stamping, and a stamp holder. The mount can be connected to the support structure through a press base. The mount can comprise components which hold the object or composition to be stamped such as, for example, one or more holding jaws. The support structure can also comprise a damping element such as a spring which provides for force and pressure measurement. As stamping is carried out, and pressure is generated and released, the pressure of stamping can be measured via the damping element. One or more measurement devices to measure pressure, temperature, time, or other experimental variables can be operably coupled to the instrument. Computers, including hardware, software, and data storage can be operably coupled to the instrument.

The composition can be a pharmaceutical composition.

More particularly, the stamping instrument can comprise (i) a stamping force application device which is adapted to be coupled to a stamp for stamping an object, a composition, or a pharmaceutical composition, (ii) a mount for holding the object, the composition, or the pharmaceutical composition to be stamped, wherein the stamping force application device and the mount for holding the object, the composition, or the pharmaceutical composition are operably connected to provide measurement of stamping conditions and relative motion for stamping. The force application device, for example, can comprise a press support structure, a pressure ram, and a ram bearing as described further below. The mount for holding the object can be adapted to provide for damping and measurement of force and pressure.

FIGS. 13-16 illustrate one embodiment of an apparatus for applying by stamping at least one identification region having at least one identification feature to pharmaceutical compositions consistent in the present invention.

Figure 13:
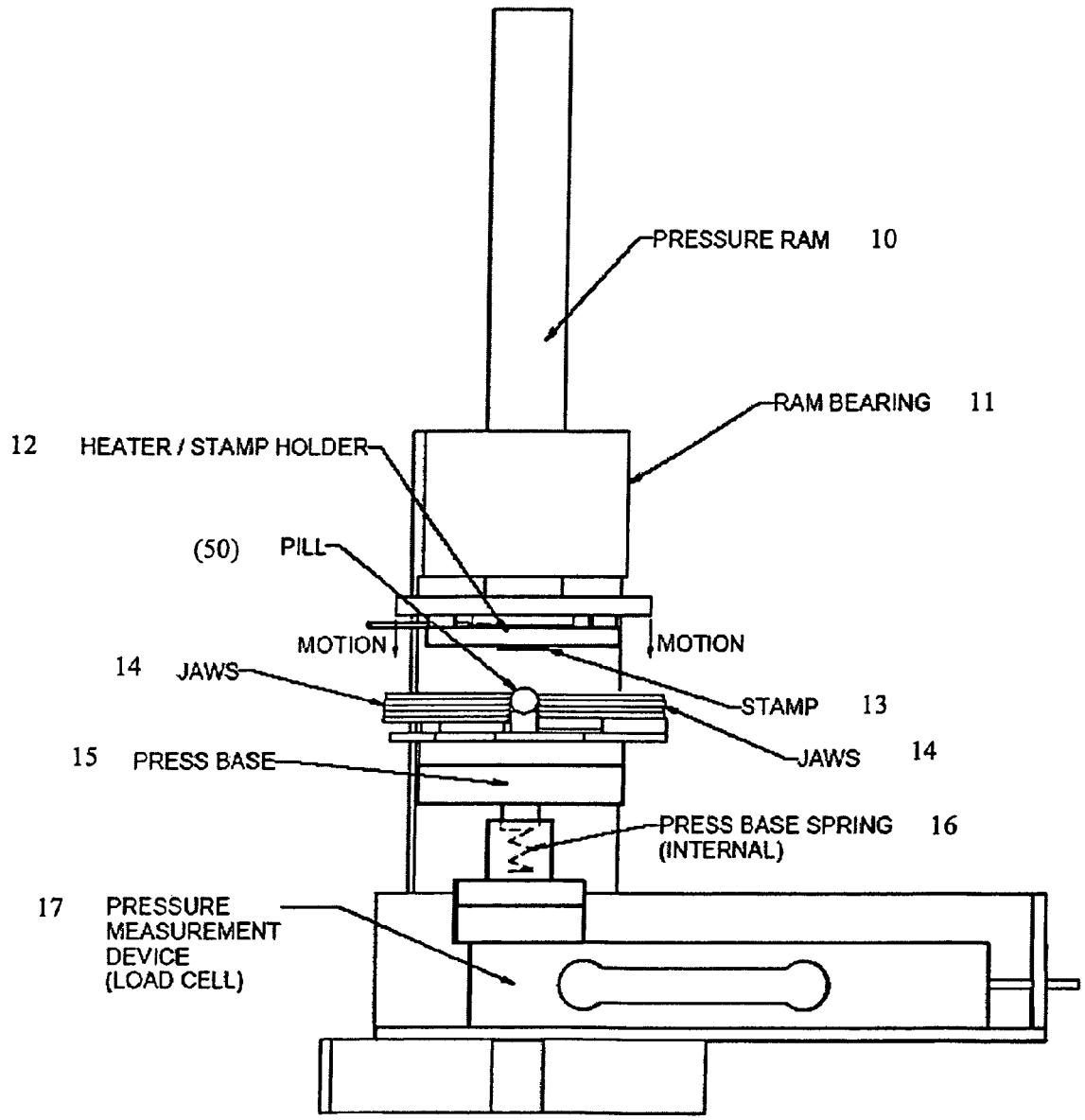
FIG. 13 shows a front view of an apparatus that may be used to apply the identification features of the present invention.

As shown in FIG. 13, the apparatus can have a pressure ram 10 housed in a ram bearing 11. A heater/stamp holder 12, which can hold the stamp 13 and heat it if desired to a desired temperature, can be connected at one end of the pressure ram 10 and can be positioned over the pharmaceutical composition to be stamped, which is shown as a pill (50). This pharmaceutical composition can be held in place by a pharmaceutical composition mount 14, which is shown as jaws, positioned under the heater/stamp holder 12.

The pharmaceutical composition mount 14, shown as jaws, can be mounted on a press base 15. This press base 15 can be in turn connected to an internal press base spring 16 and a load cell 17.

Figure 14:
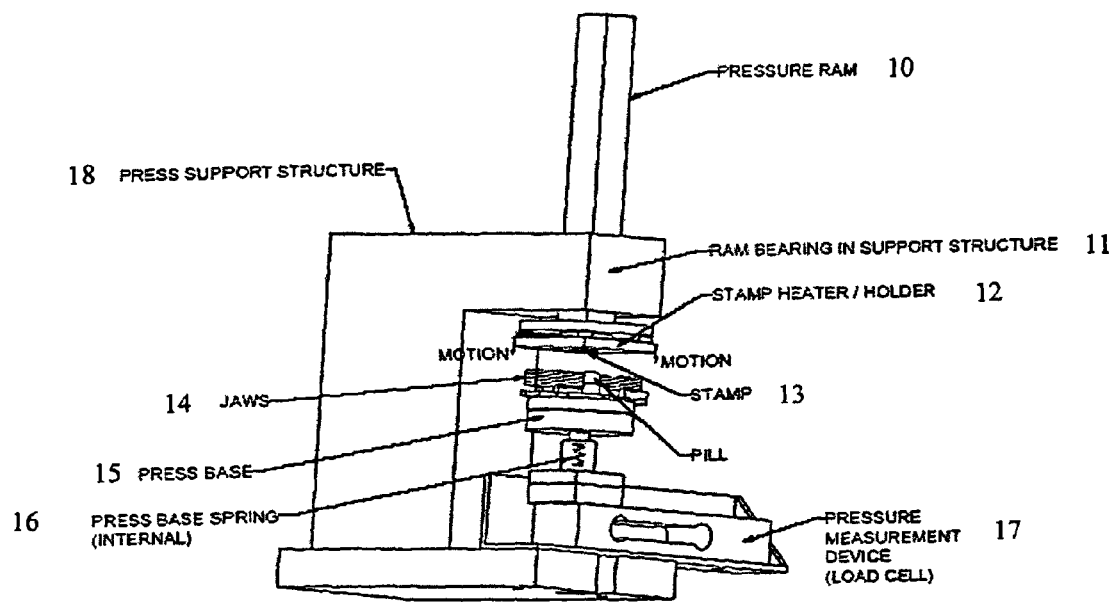
FIG. 14 shows a perspective view of the apparatus shown in FIG. 13.

The apparatus shown in FIG. 13 can be operated by moving the pressure ram 10 in a downward direction guided by the ram bearing 11, which can be part of a support structure 18 not shown directly in FIG. 13 but shown in FIG. 14. The stamp 13 mounted on the heater/stamp holder 12, which is mounted on the pressure ram 10, is thereby pushed into the pharmaceutical composition, shown as a pill, which is held by the pharmaceutical composition mount 14. The force applied to the pharmaceutical composition held by the pharmaceutical composition mount 14 compresses the internal press base spring 16. The press base spring 16 dampens the force applied to the pharmaceutical composition. The load cell 17 measures the amount of force applied to the pharmaceutical composition. Thus, the load cell 17 can be used to apply a desired and consistent amount of force to the pharmaceutical composition with a large degree of sensitivity. The heater element in 12 may be used to heat the stamp if desired to aid the stamping process.

FIG. 14 further shows in a perspective view the apparatus including the press support structure 18. which holds the ram bearing 11.

The apparatus may be operated manually by a user, or it may be operated by electronic, computer, or automatic control in a production environment. Preferably, the load cell is used to apply a consistent amount of force. Specifically, the force applied to the pharmaceutical composition preferably should be a specific amount held for some set period of time or released immediately once the predetermined force is applied. The desired force will vary depending on the pharmaceutical composition to be stamped. One skilled in the art can perform experiments to find an optimal force profile for stamping depending on the characteristics of the pharmaceutical composition being stamped. Production rate can be another important factor in selecting stamp conditions.

Figure 15:
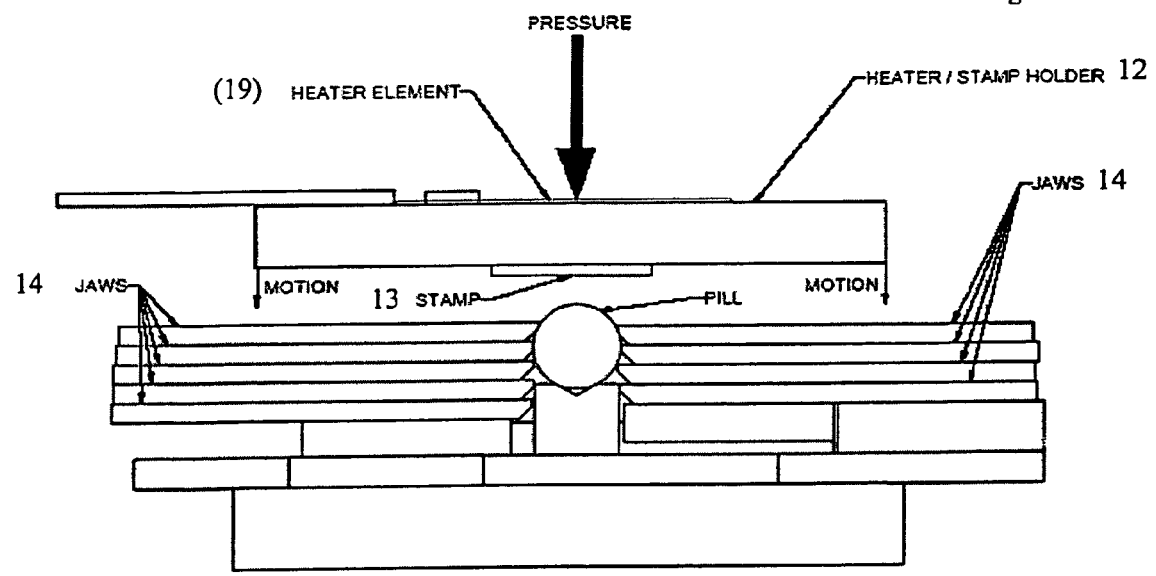
FIG. 15 shows an enlarged view of the stamp holder, stamp, and pharmaceutical form mount portions of the apparatus shown in FIG. 14.

In many circumstances, it may be desirable to use heat in combination with force to stamp. For this reason, in some embodiments, as shown in FIG. 15, the apparatus can have a heating element 19 that may be used to heat the stamp directly through the heat/stamp holder 12. FIG. 15 shows how the heating element (19) can be mounted on the heater/stamp holder to heat the stamp. Heat can also be applied to the pharmaceutical composition via an environmental chamber or via the pharmaceutical composition mount 14 which is shown as jaws in FIG. 15. Like the force, the desirability of heat and the amount and duration of heat to apply will vary with the pharmaceutical composition. Exemplary stamping temperatures and pressures are described above. One skilled in the art can perform experiments to find optimal heating conditions for stamping. Cold stamping can be carried out.

The pharmaceutical composition mount 14 may hold non-wafer form pharmaceuticals, such as cylindrical pills and capsules. FIG. 15 shows one embodiment where the pharmaceutical composition mount is constructed from parallel plates placed on top of one another. The parallel plates are split down the middle to create a space to hold a pharmaceutical form. Each of these parallel plates may be adjusted independently to hold a variety of shapes including cylinders, disks, and other non-wafer shapes. This ability to hold pharmaceutical forms of varying shapes is valuable, because pharmaceutical compositions are manufactured in a number of different forms. Any number of other mechanisms to suitably hold non-wafer pharmaceutical forms can be used by one skilled in the art and considered within the scope of the invention. Such alternative mechanisms can hold non-wafer pharmaceutical forms securely enough to allow stamping. At the same time, such alternative mechanisms should minimize damage to the pharmaceutical form. Preferably, a user can adjust the pharmaceutical composition mount to accommodate a variety of pharmaceutical forms. Such alternative mechanisms, for example, could use vacuum suction to hold the pharmaceutical form. In another embodiment a cut-out shape can be used to hold the pharmaceutical form using mechanical pressure from the stamp side.

The press base spring 16 can add sensitivity to the apparatus by dampening the force applied to the pharmaceutical form by the pressure ram. Thus, breakage and other damage to the pharmaceutical forms to be stamped may be reduced or eliminated. The tension of the spring may be selected by one skilled in the art to provide the proper amount of dampening. In some embodiments, the single spring may be replaced by multiple springs or other dampening members. For example, the single spring illustrated in FIG. 13 may be replaced by a hydraulic member in some embodiments. This hydraulic member may provide a similar dampening function as the spring illustrated in FIG. 13. The apparatus can contain dampening members readily selected by one of ordinary skill in the art to dampen the force applied to the pharmaceutical form being stamped.

Figure 16:
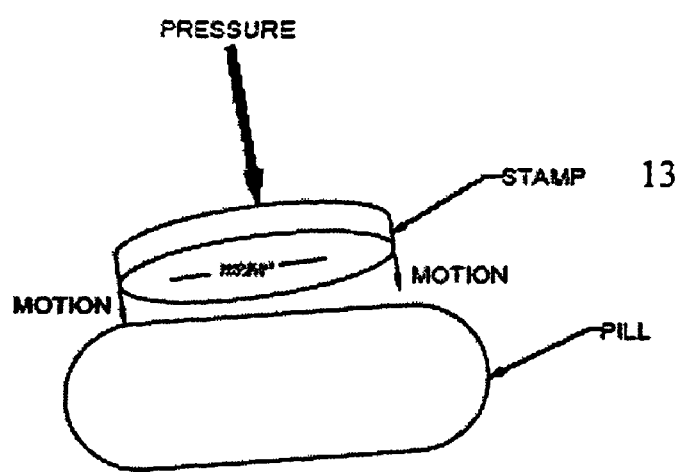
FIG. 16 shows schematic of the stamp and pharmaceutical composition during application of identification features.

FIG. 16 shows the stamp in motion to contact the pharmaceutical composition, wherein the stamp is smaller than the pharmaceutical composition.

Other modifications may be made to the apparatus described above by one of ordinary skill in the art. For example, the pharmaceutical composition mount may hold more than one pharmaceutical composition. This modification may allow multiple pharmaceutical compositions to be stamped simultaneously, or it may allow multiple pharmaceutical compositions to be stamped without needing to remount additional pharmaceutical compositions. In another embodiment, the heater/stamp holder may hold more than one stamp so that multiple pharmaceutical compositions may be stamped simultaneously. In the alternative, the multiple stamps may be used to allow a user to switch stamps without needing to manually replace the existing stamp. In another embodiment, the pressure ram or the pharmaceutical form mount may be designed to move in the x-y plane. This modification may allow pharmaceutical compositions positioned at different locations on the pharmaceutical form mount to be stamped. These and other modifications may be made by one skilled in the art and are within the scope of the present invention.

In a preferred embodiment, the instrument shown in FIGS. 13-16 comprises the stamps described above and are operated in continuous, automated mode under computer control at high production speeds.

Additional embodiments for the stamping instrument can be found in U.S. provisional patent application Ser. No. 60/637,007 filed Dec. 20, 2004 to Cruchon-Dupeyrat et al. "Apparatus and Methods for Preparing Identification Features", which is completely incorporated by reference in the present specification in its entirety including the specification, figures, and claims.

IX. Further Literature to Enable Practice of the Invention

No admission is made that any technical literature noted herein is prior art. One skilled in the art can refer to prior technical literature in the practice of the present invention and can use selected features therein in the practice of this invention.

For example, U.S. Pat. No. 5,700,998 to Palti is incorporated by reference in its entirety. It describes a drug coding and delivery system in which a machine readable code is placed on the outer surface of drug pills. The code can be a linear bar code, a radial bar code, a code on the outer peripheral edge of the tablet, or a coaxial code. In addition, U.S. Pat. No. 5,845,264 to Nelhaus is incorporated by reference in its entirety and describes bar code identification of drugs. U.S. Pat. No. 5,992,742 to Sullivan is incorporated by reference in its entirety and purports to describe an identification code which has patterns whose resolution is too small for the unaided eye to discern. U.S. Pat. No. 6,543,692 to Nelhaus et al. is incorporated by reference in its entirety. It discloses a schema for identification of solid form drugs, which include a drug identification system comprising a composite pill imprint formed of a human-readable symbol and a machine-readable bar code.

Methods of nanolithographic and microlithographic fabrication are also known including use of etching. For example, the text *Fundamentals of Microfabrication, The Science of Minitaturization*, $2^{nd}$ *Ed.*, Marc J. Madou, describes micro and nanotechnologies including additive and subtractive methods, for example, lithography (Chapter 1), pattern transfer with dry etching methods (Chapter 2), pattern transfer with additive methods (Chapter 3), and wet bulk micromachining (Chapter 4). Also, the text *Direct-Write Technologies for Rapid Prototyping Applications: Sensors, Electronics, and Integrated Power Sources* (Eds. A. Pique and D. B. Chrisey), describes micro and nanotechnologies including additive and subtractive methods. For example, bulk micromachining and etching are described on pages 617-619. DPN printing on the Sub-100 nanometer length scale is described in Chapter 10. Self-assembled monolayers, etching, and microfabrication are further described in, for example, U.S. Pat. Nos. 5,618,760 to Soh et al; 5,620,850 to Bamdad et al.; and 5,512,131 to Kumar et al.

References on stamping and molding include: (i) Harmening Bacher Bley et al. *Proceedings IEEE Micro Electro Mechanical Systems* 202 (1992), (ii) "Molding of Plastic Components Using Micro-Dem Tools", Electronics Manufacturing Technology Symposium, Hong Li and Stephen D. Senturia, 1992, pp. 145-149, and (iii) I. Rubin *Injection Molding* (Wiley, N.Y.) 1992.

All references cited in this application are incorporated by reference in their entirety.

XI. Working Examples

To further describe the invention, additional description is provided on process steps and variables including figures and working examples. The following points relate to the working examples and are important potential steps and variables in carrying out the invention:

1. Stamp Fabrication
   Substrate cleaning
   Thermal evaporation of adhesion layers such as chromium or titanium (x nm) and then a metal, e.g., gold (x nm) onto substrate using an electron beam evaporator
   DPN printing patterns on gold surface using NSCRIPTOR and InkCAD software with MHA ink
   Redundant patterns using multiple parallel pen assemblies
   Wet chemical etching to remove gold from around patterns, remove titanium
   RIE etching to create high aspect ratio patterns in the silicon
2. Optional Coating of Stamp with a Release Layer, e.g. Teflon-Like Layer, or durable coating
   Use of amorphous fluorocarbon polymer, e.g., Cytop spin on polymer
   Use of polymer, Paralene CVD coating and release layer
   Diamond-like carbon (DLC), with or without fluorine
   Nickel electroplating
3. Stamping Variables
   Stamping apparatus
   Temperature
   Time
   Pressure
4. Types of Pills Stamped:
   film coating
   liquid filled capsule
   tablet

WORKING EXAMPLES

The invention is further described with use of the following non-limiting working examples.

Nano-Embossing Pharmaceutical Tablets with Stamps Generated by DPN Printing

Experimental Section

Chemicals. Ammonium hydroxide, hydrogen peroxide (30%), 16-mercaptohexadecanoic acid (MHA), $Na_2S_2O_3$, KOH, $K_3Fe(CN)_6$ and $K_4Fe(CN)_6$. Milli-Q water (>18 MΩcm) was used for all aqueous experiments.

Substrate preparation. A silicon wafer was cut into 1×1 $cm^2$ squares. After being ultrasonicated with acetone for 10 min and rinsed with Milli-Q water, the Si substrates were immersed into a boiling solution of ammonium hydroxide and hydrogen peroxide (V($NH_4OH$):V($H_2O_2$):V($H_2O$)=1:1:5) for 1 h. The cleaned substrates were rinsed with Milli-Q water and dried with $N_2$, and then put into a Varian Electron Beam Evaporator (UIC) chamber. Under vacuum conditions (pressure<$10^{-7}$ Torr), the substrates were coated with a 1 nm Ti adhesion layer via thermal evaporation and subsequently coated with Au (10 nm) to make Au film.

Dip-pen nanolithography (DPN Printing) and wet chemical etching. The metal substrates were patterned with 16-mercaptohexadecanoic acid (MHA) by DPN printing, and all DPN printing experiments were carried out under ambient conditions (probe set point=0.5 nN, 22-24° C., 30-36% relative humidity) by using a NSCRIPTOR™ (NanoInk Inc., Chicago, Ill.) with MHA-coated tips. MHA-coated tips were prepared by immersing $Si_3N_4$ DPN parallel 3-probe assembly (k=0.004, 0.016, and 0.032 N/m for probes with the s-3, s-4 and s-5 model number, respectively, NanoInk Inc., Chicago, Ill.) in an acetonitrile solution saturated with MHA for ~5 s. They were subsequently dried with compressed difluoroethane (Dust-off, Ted Pella, Inc., Redding, Calif.). A2-A11 cantilevers from NanoInk also were used. Multiple dipping including double dipping processes were used in some cases to coat the probes.

The Au substrates, patterned with MHA, were immersed in a ferri/ferrocyanide etching solution (a 1:1:1:1 (v:v:v:v) aqueous mixture of 0.1 M $Na_2S_2O_3$, 1.0 M KOH, 0.01 M $K_3Fe(CN)_6$ and 0.001 M $K_4Fe(CN)_6$) for ~10 min under constant stirring to remove the Au layer from the exposed regions of the Au substrate. After rinsing with Milli-Q $H_2O$, the etched substrates were dried with $N_2$.

Technical literature including experimental descriptions for these processes can be found in the following references which are hereby incorporated by reference in their entirety: (a) Zhang, H.; Li, Z.; Mirkin, C. A. *Adv. Mater.* 2002, 14, 1472. (b) Zhang, H.; Chung, S. W.; Mirkin, C. A. *Nano Lett.* 2003, 3, 43. (c) Zhang, H.; Lee, K. B.; Li, Z.; Mirkin, C. A. *Nanotechnology* 2003, 14, 1113. (d) Zhang, H.; Mirkin, C. A. *Chem. Mater.* Web Release Date: 24 Mar. 2004; (Article) DOI: 10.1021/cm0305507.

AFM images. All etched metal nanostructures were imaged under ambient conditions in contact mode using a NSCRIPTOR™ (NanoInk Inc., Chicago, Ill.) or an Auto-Probe CP AFM (TM Microscopes, Sunnyvale, Calif.) with a DPN $Si_3N_4$ probe (model s-1, k=0.041 N/m, NanoInk Inc., Chicago, IL).

Reactive Ion Dry Etching. The patterned dice were processed as follows: the wafers were etched for 1.5 minutes in a Technics Micro RIE with 4 sccm SF6 gas at an RF Power=100 Watts. The pressure was ~70-100 mT (uncontrolled).

Release Layer Coatings. Some of the samples were coated with fluorocarbon using a STS DRIB (deep reactive ion etching) system operating with 85 sccm C4F8 and 8.5 sccm Ar gases for 16 seconds under the following conditions: Platten power (substrate RF bias)=30 Watts, coil power (ICP)=600 watts, APC (throttle valve position)=67 degrees.

Figure 12:
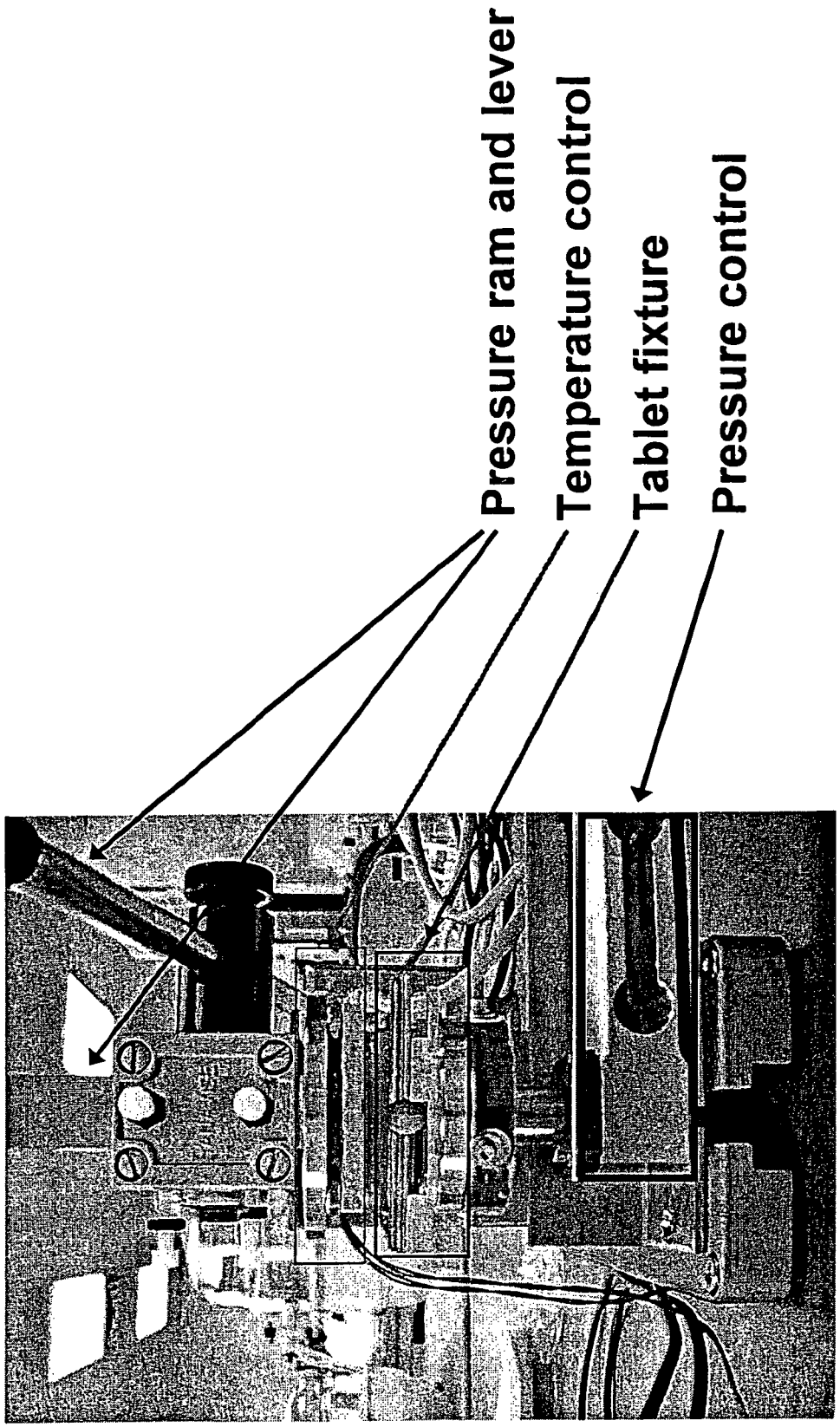
FIG. 12 shows a front view of the apparatus used to test temperature, time, and pressure of stamping process.

Stamping. Using the apparatus shown in FIG. 12, various pill surfaces were imprinted with a silicon stamp. Time for stamping, pressure, and temperature were optimized by stamping under a range of conditions (Time=0.5 s to 30 s, T=60° C. to 130° C., Pressure=1 MPa to 27 MPa).

(2) Results

Results. Silicon stamps were imaged by SEM and AFM after reactive ion etching. Stamps had relatively smooth surfaces with relief structures making up the pattern, as shown in FIGS. 1-3. The stamps were used without further treatment to imprint film-coated tablets and soft, liquid-filled tablets, using a range of temperature, pressure, and time during stamping in order to find the optimal conditions for an imprint. After stamping pills were examined using optical microscopy and atomic force microscopy. The optimal conditions for film-coated tablets were as follows: time=1 to 3 s, Temp=100-110° C., pressure=5-10 MPa. For soft, liquid-filled caplets, the optimal conditions were as follows: time=3 s, Temp=80C, and Pressure=13 MPa.

After finding the optimal stamping conditions, the imprint patterns on the stamped pills were imaged with AFM and the line dimensions in the barcode patterns were compared to the dimensions of the original silicon master. The line widths and depths matched closely the original stamp pattern. However, since there was particulate matter on the pill surface, it was decided to scan more than one of the patterned regions to obtain a complete pattern.

Finally, additional numbered embodiments described in priority provisional application Ser. No. 60/563,443 filed Apr. 20, 2004 include:

1. A pharmaceutical composition comprising: a pharmaceutical composition having a surface, wherein the surface comprises at least one identification region, the region having at least one identification feature, the feature having a lateral dimension of about 500 microns or less.
2. The pharmaceutical composition according to 1, wherein the lateral dimension is about 10 microns or less.
3. The pharmaceutical composition according to 1, wherein the lateral dimension is about one micron or less.
4. The pharmaceutical composition according to 1, wherein the lateral dimension is about 500 nm or less.
5. The pharmaceutical composition according to 1, wherein the lateral dimension is about 100 nm or less.
6. The pharmaceutical composition according to 1, wherein the identification feature has a height dimension of about one micron or less.
7. The pharmaceutical composition according to 1, wherein the identification feature has a height dimension of about 500 nm or less.
8. The pharmaceutical composition according to 1, wherein the identification feature has a height dimension of about 250 nm or less.
9. The pharmaceutical composition according to 1, comprising a plurality of identification features which are separated from each other by an average distance of about 100 microns or less.
10. The pharmaceutical composition according to 1, comprising a plurality of identification features which are separated from each other by an average distance of about 10 microns or less.
11. The pharmaceutical composition according to 1, comprising a plurality of identification features which are separated from each other by an average distance of about one micron or less.
12. The pharmaceutical composition according to 1, comprising a plurality of features which are separated from each other by an average distance of about 500 nm or less.
13. The pharmaceutical composition according to 1, wherein the identification region is about 10,000 square microns or less.
14. The pharmaceutical composition according to 1, wherein the identification region is about 400 square microns or less.
15. The pharmaceutical composition according to 1, wherein the identification region is about 4 square microns or less.
16. The pharmaceutical composition according to 1, wherein the identification feature comprises an indentation into the surface.
17. The pharmaceutical composition according to 1, wherein the identification feature comprises a protrusion out from the surface.
18. The pharmaceutical composition according to 1, wherein the identification region comprises at least one indentation into the surface and at least one protrusion out from the surface.
19. The pharmaceutical composition according to 1, wherein the identification region comprises a bar code.
20. The pharmaceutical composition according to 1, wherein the identification region comprises a hologram.
21. The pharmaceutical composition according to 1, wherein the identification feature is a dot.
22. The pharmaceutical composition according to 1, wherein the identification feature is a line.
23. The pharmaceutical composition according to 1, wherein the surface further comprises at least one mark outside of the identification region which is detectable by optical microscopy.
24. The pharmaceutical composition according to 1, wherein the pharmaceutical composition is a pill, tablet, or capsule.
25. The pharmaceutical composition according to 1, comprising a plurality of identification regions each having a plurality of identification features which are separated from each other by an average distance of about 100 microns or less, wherein the plurality of identification features have an average lateral dimension of about one micron or less, and an average height dimension of about one micron or less.
26. The pharmaceutical composition according to 1, comprising a plurality of identification features which are separated from each other by an average distance of about 10 microns or less, wherein the plurality of identification features have an average lateral dimension of about 500 nm or less, and an average height dimension of about 500 nm or less.
27. The pharmaceutical composition according to 1, comprising a plurality of identification features which are separated from each other by an average distance of about 1 micron or less, wherein the plurality of identification features have an average lateral dimension of about 100 nm or less, and an average height dimension of about 250 nm or less.
28. The pharmaceutical composition according to 1, wherein the identification region comprises identification features which form a hologram or bar code, and the surface further comprises at least one mark outside the identification region which is detectable by optical microscopy.
29. The pharmaceutical composition according to 1, wherein the identification region comprises identification features which form a hologram or bar code, and the surface further comprises at least one mark outside the identification region which is detectable my optical microscopy.
30. The pharmaceutical composition according to 1, wherein the identification region comprises identification features which form a hologram or bar code.
31. An object comprising:
    an object having a surface, wherein the surface comprises at least one identification region, the region having at least one identification feature, the feature having a lateral dimension of about 500 microns or less.
32. The object according to 31, wherein the lateral dimension is about one micron or less.
33. The object according to 31, wherein the identification feature has a height dimension of about one micron or less.
34. The object according to 31, wherein the identification feature has a height dimension of about 250 nm or less.
35. The object according to 31, comprising a plurality of identification features which are separated from each other by an average distance of about 100 microns or less.

36. The object according to 31, wherein the identification region is about 10,000 square microns or less.

37. The object according to 31, wherein the identification feature comprises an indentation into the surface.

38. The object according to 31, wherein the identification feature comprises a protrusion out from the surface.

39. The object according to 31, wherein identification region comprises identification features which form a bar code.

40. The object according to 31, wherein identification region comprises identification features which form a hologram.

41. A composition comprising:
a composition having a surface, wherein the surface comprises at least one identification region, the region having at least one identification feature, the feature having a lateral dimension of about 500 microns or less.

42. The composition according to 41, wherein the lateral dimension is about one micron or less.

43. The composition according to 41, wherein the identification feature has a height dimension of about one micron or less.

44. The composition according to 41, wherein the identification feature has a height dimension of about 250 nm or less.

45. The composition according to 41, comprising a plurality of identification features which are separated from each other by an average distance of about 100 microns or less.

46. The composition according to 41, wherein the identification region is about 10,000 square microns or less.

47. The composition according to 41, wherein the identification feature comprises an indentation into the surface.

48. The composition according to 41, wherein the identification feature comprises a protrusion out from the surface.

49. The composition according to 41, wherein identification region comprises identification features which form a bar code.

50. The composition according to 41, wherein identification region comprises identification features which form a hologram.

51. A method of making a pharmaceutical composition having at least one identification region and at least one identification feature comprising: (i) providing a stamp which has a surface to form at least one identification region having at least one identification feature; (ii) providing a pharmaceutical composition having a surface; and (iii) contacting the stamp and the pharmaceutical composition under conditions so that the pharmaceutical composition comprises a surface having the at least one identification region having at least one identification feature.

52. The method according to 51, wherein the contacting is carried out at a temperature of about 25° C. to about 400° C.

53. The method according to 51, wherein the contacting is carried out at a pressure of about 0.01 MPa to about 1,000 MPa.

54. The method according to 51, wherein the contacting is carried out for a time of about 0.1 seconds to about 50 seconds.

55. The method according to 51, wherein the contacting is carried out for a time of about 0.1 seconds to about 50 seconds, at a pressure of about 0.01 MPa to about 1,000 MPa, and at a temperature of about 25° C. to about 400° C.

56. The method according to 51, wherein the identification feature has a lateral dimension of about 500 microns or less.

57. The method according to 51, wherein the identification feature has a lateral dimension of about one micron or less.

58. The method according to 51, wherein the identification feature has a height dimension of about one micron or less.

59. The method according to 51, wherein the identification feature, has a height, dimension of about 250 nm or less.

60. The method according to 51, wherein the pharmaceutical composition comprises a plurality of identification features which are separated from each other by an average distance of about 100 microns or less.

61. The method according to 51, wherein the identification region is about 10,000 square microns or less.

62. The method according to 51, wherein the identification feature comprises an indentation into the surface.

63. The method according to 51, wherein the identification feature comprises a protrusion out from the surface.

64. The method according to 51, wherein identification region comprises a bar code.

65. The method according to 51, wherein identification region comprises a hologram.

66. A method of making a composition having at least one identification region and at least one identification feature without etching after formation of identification feature consisting essentially of: (i) providing a stamp which has a surface to form at least one identification region having at least one identification feature; (ii) providing a composition having a surface; and (iii) contacting the stamp and the composition under conditions so that the composition comprises a surface having the at least one identification region having at least one identification feature.

67. The method according to 66, wherein the contacting is carried out at a temperature of about 25° C. to about 400° C.

68. The method according to 66, wherein the contacting is carried out at a pressure of about 0.01 MPa to about 1,000 MPa.

69. The method according to 66, wherein the contacting is carried out for a time of about 0.1 seconds to about 50 seconds.

70. The method according to 66, wherein the contacting is carried out for a time of about 0.1 seconds to about 50 seconds, at a pressure of about 0.01 MPa to about 1,000 MPa, and at a temperature of about 25° C. to about 400° C.

71. The method according to 66, wherein the identification feature has a lateral dimension of about 500 microns or less.

72. The method according to 66, wherein the identification feature has a lateral dimension of about one micron or less.

73. The method according to 66, wherein the identification feature has a height dimension of about one micron or less.

74. The method according to 66, wherein the identification feature has a height dimension of about 250 nm or less.

75. The method according to 66, wherein the pharmaceutical composition comprises a plurality of identification features which are separated from each other by an average distance of about 100 microns or less.

76. The method according to 66, wherein the identification region is about 10,000 square microns or less.

77. The method according to 66, wherein the identification feature comprises an indentation into the surface.

78. The method according to 66, wherein the identification feature comprises a protrusion out from the surface.

79. The method according to 66, wherein identification region comprises a bar code.

80. The method according to 66, wherein identification region comprises identification features which form a hologram.

81. An apparatus for forming identification features to pharmaceutical compositions comprising:
- a pressure ram;
- optionally, a stamp attached to the pressure ram for imprinting at least one identification feature on a pharmaceutical composition;
- a mount for holding at least one non-wafer pharmaceutical composition; and
- a load cell for measuring the amount of force applied to the at least one pharmaceutical composition;
- wherein the pressure ram presses the stamp against the at least one pharmaceutical composition held by the pharmaceutical composition mount with a desired amount of force as measured by the load cell to form at least one identification feature on the at least one pharmaceutical composition.

82. The apparatus of 81, further comprising a dampening member connected to the pharmaceutical form mount.

83. The apparatus of 81, further comprising a heating element in thermal contact with the stamp.

84. The apparatus of 81, further comprising a heating element in thermal contact with the at least one pharmaceutical composition.

85. The apparatus of 81, wherein the pressure ram may be moved in the x-y plane.

86. The apparatus of 81, wherein the stamp imprints more than one identification feature.

87. The apparatus of 81, wherein the pharmaceutical form mount holds more than one pharmaceutical composition.

88. The apparatus of 81, wherein the pharmaceutical composition mount may be moved in the x-y plane.

89. A pharmaceutical composition comprising:
a pharmaceutical composition having a surface, wherein the surface comprises at least one identification region, the region having a plurality of identification line features, the lines having a line width of about one micron or less and a line length of at least one micron.

90. The pharmaceutical composition according to 89, wherein the line width is about 500 nm or less and the line length is at least 10 microns.

91. The pharmaceutical composition according to 89, wherein the line width is about 200 nm or less and the line length is at least one micron.

92. A stamping instrument comprising: (i) a device adapted for coupling with a stamp, and (ii) a mount for holding an object or composition, wherein the device and the mount are operably coupled for relative motion of the stamp and the object or composition and for stamping the object or composition with the stamp.

93. The instrument according to 92, further comprising components for bringing the object or composition to the mount for stamping, and components for bringing the object or composition away from the mount after stamping.

While it is apparent that the preferred embodiments of the inventions disclosed herein provide the advantages and features noted above, it should be appreciated by one of skill in the art that the invention is susceptible to modification, variation and change without departing from the proper scope or fair meaning of the following claims.

What is claimed is:

1. A composition comprising:
a pharmaceutical composition having a surface, wherein the surface comprises a visible stamped surface impression which is smooth and reflective and comprises a plurality of identification regions, the identification regions being areas on the surface in which a plurality of identification features forming a pattern are stamped into the surface,
wherein at least two of the identification regions comprise the same pattern of stamped identification features of the at least two identification regions,
wherein the identification features are nanoscale indentations in the surface of the pharmaceutical composition, or nanoscale protrusions from the surface of the pharmaceutical composition,
wherein the stamped identification features have a lateral dimension of about one micron or less and are not individually visible with the naked eye,
wherein the identification regions have an area of about 10,000 square microns or less, and
wherein the identification features do not comprise added chemicals.

2. The composition according to claim 1, wherein the lateral dimension is about 500 nm or less.

3. The composition according to claim 1, wherein the lateral dimension is about 100 nm or less.

4. The composition according to claim 1, wherein the identification features have a height dimension of about five microns or less.

5. The composition according to claim 1, wherein the identification features have has a height dimension of about one micron or less.

6. The composition according to claim 1, wherein the identification features have has a height dimension of about 500 nm or less.

7. The composition according to claim 1, wherein the identification features have has a height dimension of about 250 nm or less.

8. The composition according to claim 1, wherein the identification features are separated from each other by an average distance of about 10 microns or less.

9. The composition according to claim 1, wherein the identification features are separated from each other by an average distance of about one micron or less.

10. The composition according to claim 1, wherein the identification features are separated from each other by an average distance of about 500 nm or less.

11. The composition according to claim 1, wherein the identification regions have an area of about 400 square microns or less.

12. The composition according to claim 1, wherein the identification regions have an area of about 4 square microns or less.

13. The composition according to claim 1, wherein the identification features are indentations in the surface of the pharmaceutical composition.

14. The composition according to claim 1, wherein the identification features are protrusions from the surface of the pharmaceutical composition.

15. The composition according to claim 1, wherein at least one of the identification features is an indentation in the surface of the pharmaceutical composition, and at least one of the identification features is a protrusion from the surface of the pharmaceutical composition.

16. The composition according to claim 1, wherein the at least two of the identification regions each comprise a bar code.

17. The composition according to claim 1, wherein the least two of the identification regions each comprise a hologram.

18. The composition according to claim 1, wherein at least one of the identification features has a shape of a dot or a line.

19. The composition according to claim 1, wherein the identification regions do not extend around a full circumference of the pharmaceutical article.

20. The composition according to claim 1, wherein the surface further comprises at least one mark outside of the identification regions which is detectable by optical microscopy.

21. The composition according to claim 1, wherein the surface further comprises at least one mark outside of the identification regions which is detectable by optical microscopy and which has a lateral dimension of about 800 microns or less.

22. The composition according to claim 1, wherein the pharmaceutical composition is a pill, caplet, tablet, or capsule.

23. The composition according to claim 1, comprising more than twenty of the identification regions each having a plurality of identification features which are separated from each other by an average distance of about 100 microns or less, and wherein the identification features have an average height dimension of about one micron or less.

24. The composition according to claim 1, wherein the identification regions comprise identification features which form a hologram or bar code, and the surface further comprises at least one mark which is detectable by optical microscopy.

* * * * *

UNITED STATES PATENT AND TRADEMARK OFFICE
CERTIFICATE OF CORRECTION

| | | |
|---|---|---|
| PATENT NO. | : 8,235,302 B2 | Page 1 of 1 |
| APPLICATION NO. | : 11/109877 | |
| DATED | : August 7, 2012 | |
| INVENTOR(S) | : Cedric Loiret-Bernal et al. | |

It is certified that error appears in the above-identified patent and that said Letters Patent is hereby corrected as shown below:

Claim 1, Column 30, lines 2-3, delete "of the at least two identification regions"

Signed and Sealed this
Thirteenth Day of November, 2012

David J. Kappos
*Director of the United States Patent and Trademark Office*